(12) United States Patent
Watanabe

(10) Patent No.: US 12,419,571 B2
(45) Date of Patent: Sep. 23, 2025

(54) SKIN EVALUATION DEVICE, SKIN EVALUATION SYSTEM, SKIN EVALUATION METHOD, AND NON-TRANSITORY COMPUTER-READABLE RECORDING MEDIUM STORING PROGRAM FOR SKIN EVALUATION

(71) Applicant: Panasonic Intellectual Property Management Co., Ltd., Osaka (JP)

(72) Inventor: Hisashi Watanabe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 626 days.

(21) Appl. No.: 17/076,884

(22) Filed: Oct. 22, 2020

(65) Prior Publication Data
US 2021/0038144 A1    Feb. 11, 2021

Related U.S. Application Data

(63) Continuation of application No. PCT/JP2019/021281, filed on May 29, 2019.

(30) Foreign Application Priority Data

Jun. 21, 2018  (JP) .................................. 2018-117616

(51) Int. Cl.
  *A61B 5/00*       (2006.01)
(52) U.S. Cl.
  CPC ............ *A61B 5/441* (2013.01); *A61B 5/0004* (2013.01); *A61B 5/002* (2013.01); *A61B 5/0077* (2013.01); *A61B 5/7225* (2013.01); *A61B 5/742* (2013.01)

(58) Field of Classification Search
  CPC ..... A61B 5/0004; A61B 5/002; A61B 5/0077; A61B 5/7225; A61B 5/742; A61B 5/44–445
  See application file for complete search history.

(56) References Cited

U.S. PATENT DOCUMENTS

2008/0194928 A1    8/2008  Bandic et al.
2009/0080726 A1    3/2009  Cotton et al.
(Continued)

FOREIGN PATENT DOCUMENTS

CN    101686819 A     3/2010
JP     7-323013      12/1995
(Continued)

OTHER PUBLICATIONS

International Search Report of PCT application No. PCT/JP2019/021281 dated Aug. 27, 2019.
(Continued)

*Primary Examiner* — Tse W Chen
*Assistant Examiner* — Evelyn Grace Park
(74) *Attorney, Agent, or Firm* — Rimon P.C.

(57) ABSTRACT

A skin evaluation device includes: a light source that projects a dot pattern created by first light onto a skin of at least one user; an image sensor that generates and outputs image data which indicates an image of the skin onto which the dot pattern is projected; a memory that stores reference data to evaluate a condition of the skin; and an arithmetic circuit that generates and outputs data related to the condition of the skin based on the image data and the reference data.

15 Claims, 15 Drawing Sheets

(56) References Cited

U.S. PATENT DOCUMENTS

| | | | |
|---|---|---|---|
| 2009/0080727 A1 | 3/2009 | Cotton et al. | |
| 2011/0002519 A1* | 1/2011 | Tomisaki | A61B 6/12 |
| | | | 382/131 |
| 2013/0023966 A1* | 1/2013 | Depfenhart | A61B 18/203 |
| | | | 607/89 |
| 2013/0329031 A1* | 12/2013 | Miura | G06V 40/145 |
| | | | 348/77 |
| 2014/0121527 A1* | 5/2014 | Adler, Jr. | A61B 5/0036 |
| | | | 600/473 |
| 2015/0374306 A1* | 12/2015 | Gelbman | G06V 40/171 |
| | | | 600/476 |
| 2016/0358011 A1 | 12/2016 | Watanabe | |
| 2016/0358332 A1 | 12/2016 | Watanabe | |
| 2017/0360303 A1* | 12/2017 | Kim | A61B 5/7278 |
| 2018/0153422 A1 | 6/2018 | Watanabe | |
| 2019/0133513 A1* | 5/2019 | Patwardhan | G06T 5/008 |
| 2019/0269363 A1* | 9/2019 | Vilenskii | A61B 5/444 |
| 2020/0138360 A1* | 5/2020 | Fan | A61B 5/441 |
| 2020/0279126 A1* | 9/2020 | Nie | G06T 7/90 |
| 2021/0038144 A1 | 2/2021 | Watanabe | |

FOREIGN PATENT DOCUMENTS

| | | |
|---|---|---|
| JP | 8-308634 A | 11/1996 |
| JP | 2002-224049 | 8/2002 |
| JP | 2002-269211 | 9/2002 |
| JP | 2003-093351 | 4/2003 |
| JP | 2009-075109 A | 4/2009 |
| JP | 2009-101218 | 5/2009 |
| JP | 2009-240644 | 10/2009 |
| JP | 2010-061689 | 3/2010 |
| JP | 2010-119428 | 6/2010 |
| JP | 2010-233584 A | 10/2010 |
| JP | 2014-033944 | 2/2014 |
| JP | 2015-221218 | 12/2015 |
| JP | 2017-000742 | 1/2017 |
| JP | 2017-000743 | 1/2017 |
| JP | 2017-213113 | 12/2017 |
| JP | 2018-054448 | 4/2018 |
| JP | 2018-089369 | 6/2018 |
| WO | WO2008086311 A2 | 7/2008 |
| WO | 2019/244586 A1 | 12/2019 |

OTHER PUBLICATIONS

English Translation of Chinese Search Report dated Aug. 3, 2024 for the related Chinese Patent Application No. 201980018582.7.

English Translation of Chinese Search Report dated Nov. 4, 2024 for the related Chinese Patent Application No. 201980018582.7.

* cited by examiner

SKIN EVALUATION DEVICE, SKIN EVALUATION SYSTEM, SKIN EVALUATION METHOD, AND NON-TRANSITORY COMPUTER-READABLE RECORDING MEDIUM STORING PROGRAM FOR SKIN EVALUATION

BACKGROUND

1. Technical Field

The present disclosure relates to a skin evaluation device, a skin evaluation system, a skin evaluation method, and a non-transitory computer-readable recording medium storing a program for skin evaluation.

2. Description of the Related Art

Due to growing trend of anti-aging, evaluation of skin condition has been increasingly important. This is because evaluation of skin condition helps improve skin condition. Thus, for instance, as described in Japanese Unexamined Patent Application Publication No. 2009-240644, Japanese Patent Nos. 4799628 and 6029379, various types of measurements of skin are being conducted in a research institute such as a university, and a cosmetic product manufacturer.

As described later, conventional measurement devices are large in size and expensive, and measurements are made by skilled technicians.

SUMMARY

One non-limiting and exemplary embodiment provides a technique for evaluating the skin condition of a user on a regular basis by a relatively inexpensive device.

In one general aspect, the techniques disclosed here feature a skin evaluation device including: a light source that projects a dot pattern created by first light onto a skin of at least one user; an image sensor that generates and outputs image data which indicates an image of the skin onto which the dot pattern is projected; a memory that stores reference data to evaluate a condition of the skin; and an arithmetic circuit that generates and outputs data related to the condition of the skin based on the image data and the reference data.

The technique of the present disclosure enables evaluation of the skin condition of a user on a regular basis by a relatively inexpensive device.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
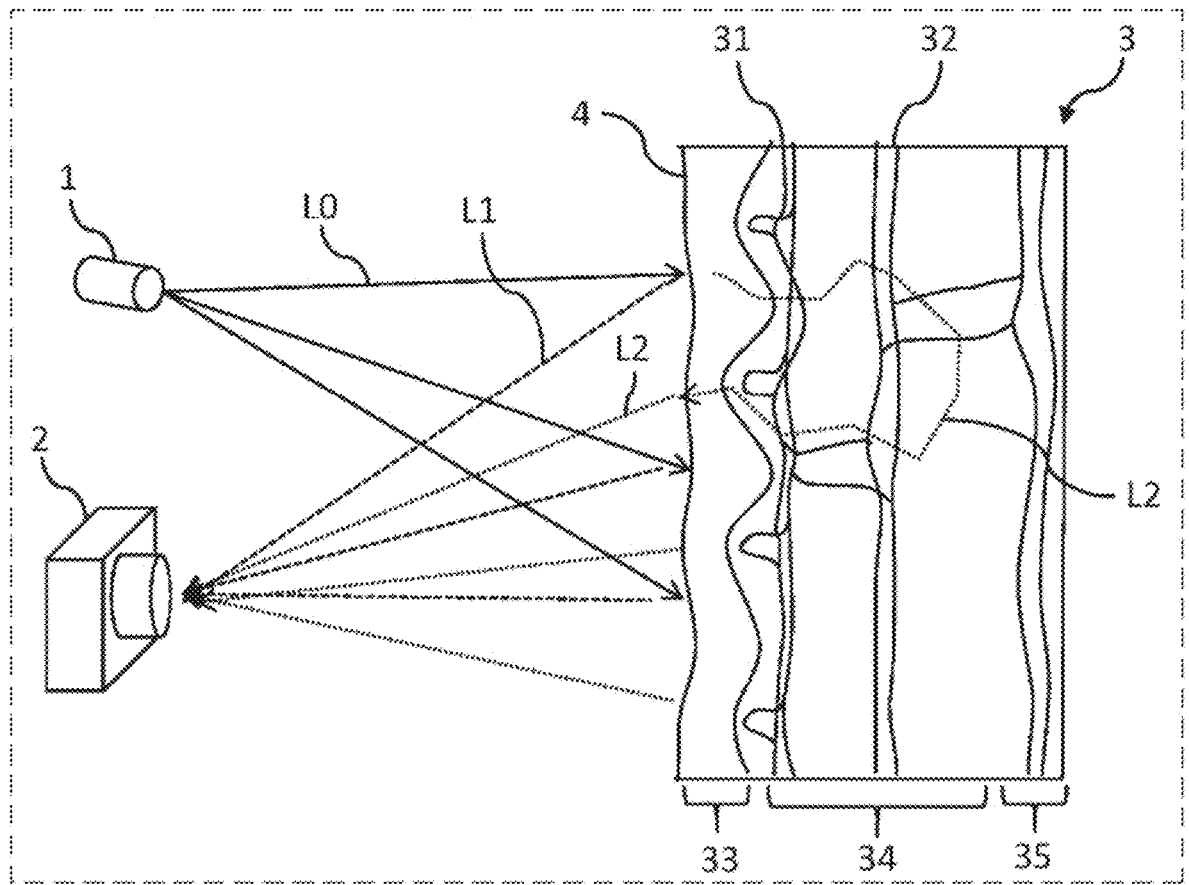
FIG. 1A is an illustration for explaining the principle for evaluating skin condition.

The underlying knowledge forming the basis of the present disclosure will be described before an embodiment of the present disclosure is described.

As words representing the texture of skin, various sensual expressions such as, fineness, dullness, turbidity, transparency, gloss, freshness of skin, are used. It is not clear how physical properties of skin or optical properties of skin correspond to the texture of skin. Thus, in a research institute such as a university, and a cosmetic product manufacturer, research for finding parameters that determine the texture of skin has been made by organoleptic examination based on various measurements of skin. The summary of the research shows that beautiful skin, in other words, fresh skin with no dullness has the following characteristics:

(Characteristics 1) high reflection rate of light from a deep part of skin, called dermis, and not from the surface of skin, called epidermis.

(Characteristics 2) uniform reflection in all directions.

These characteristics suggest that intense diffuse reflection within the dermis is an important characteristic of beautiful skin. Thus, this indicates that skin condition can be evaluated by measuring a scattering coefficient within the dermis.

Various theories have been proposed as to the origin of light scattering within a human body such as skin. Scattering within a human body occurs due to a difference between the indexes of refraction within a human body. For instance, the scattering is probably caused by (1) cellular membranes, (2) subcellular organelles such as mitochondria and golgi bodies, or (3) collagen fiber. The inventor believes that the most affecting factor to the texture of skin between these factors is scattering by collagen fiber. It is known that along with exposure to ultraviolet rays and/or aging, collagen is hardened and the amount of collagen is reduced. Accordingly, the dermis layer decreases in thickness. The state of collagen can be estimated by measuring the scattering coefficient of the dermis layer. Thus, the skin condition can be evaluated with high accuracy.

Various attempts have been made so far to evaluate skin condition from the state of diffusion of light within the skin. For instance, Japanese Unexamined Patent Application Publication No. 2009-240644 and Japanese Patent No. 4799628 disclose a measurement device that allows its opening to be brought into contact with a skin and irradiates the skin with light through the opening. The measurement device described in Japanese Unexamined Patent Application Publication No. 2009-240644 removes the light directly reflected by the surface of a skin by disposing a shielding plate near the opening inside the device. Thus, the light diffused within the skin is received. The measurement device described in Japanese Patent No. 4799628 measures diffuse reflection light by changing a measurement area. Such contact measurement devices have a problem in that the devices give unpleasant feeling to a user at the time of measurement. There is also another problem in that only information on part of skin in contact with the senor is obtained, and it is difficult to evaluate the skin condition in a wider area.

In contrast, a method of evaluating skin condition in a non-contact manner has been proposed. For instance, Japanese Patent No. 6029379 discloses a method of receiving the light diffused inside the skin by capturing the surroundings of patterned light projected onto the skin. In the method described in Japanese Patent No. 6029379, the patterned light is projected onto the skin with high accuracy in order to obtain high measurement accuracy. The intensity of the reflection light from the skin quickly decreases as the reflection light is away from the light projected. An expensive optical system is used to project patterned light and capture the reflection light.

Conventional measurement devices are large in size and expensive. In addition, at the time of measurement, a skilled technician strictly adjusts an optical system in a measurement device. Due to these reasons, the conventional measurement devices have been utilized only in a cosmetic product manufacturer and a research institute. Thus, simple and inexpensive skin evaluation device and skin evaluation method are highly demanded, which can be used easily by a general user in daily life and can evaluate the skin condition.

Based on the discussion above, the inventor has devised a skin evaluation device, a skin evaluation system, a skin evaluation method, and a non-transitory computer-readable recording medium storing a program for skin evaluation which are described in the following items.

Item 1

A skin evaluation device according to a first item includes: a light source that projects a dot pattern created by first light onto a skin of at least one user; an image sensor that generates and outputs image data which indicates an image of the skin onto which the dot pattern is projected; a memory that stores reference data to evaluate a condition of the skin; and an arithmetic circuit that generates and outputs data related to the condition of the skin based on the image data and the reference data.

Item 2

In the skin evaluation device according to the first item, the data related to the condition of the skin may be related to the condition of the skin within a dermis of the at least one user.

Item 3

In the skin evaluation device according to the first item or the second item, the arithmetic circuit may generate a characteristic data that characterizes the condition of the skin, from a relationship between a pixel value in at least a partial area in the image indicated by the image data and a number of pixels having the pixel value in the at least a partial area, and may compare the characteristic data with the reference data, and generates and outputs the data related to the condition of the skin.

Item 4

In the skin evaluation device according to the third item, when a curve of a frequency distribution showing the relationship between the pixel value and the number of pixels is fitted by a first gaussian distribution, a second gaussian distribution, and a third gaussian distribution, an average value of the second gaussian distribution may be greater than an average value of the first gaussian distribution, and less than an average value of the third gaussian distribution, and the characteristic data may indicate a value of a standard deviation of the second gaussian distribution.

Item 5

In the skin evaluation device according to the fourth item, the at least one user may include a plurality of users, the reference data may indicate a plurality of standard deviations obtained from the plurality of users, each of the plurality of standard deviations may be obtained by a same calculation as used to obtain the standard deviation of the at least one user.

Item 6

In the skin evaluation device according to the fourth item, the reference data may indicate a previously obtained value of the standard deviation of the at least one user.

Item 7

In the skin evaluation device according to the third item, the characteristic data may indicate a value of dispersion in a cumulative frequency distribution which shows a relationship between the pixel value and a cumulative number of pixels having a value lower than or equal to the pixel value in the at least a partial area.

Item 8

In the skin evaluation device according to the seventh item, the at least one user may include a plurality of users, the reference data may indicate a plurality of dispersions in a plurality of cumulative frequency distributions obtained from the plurality of users, and each of the plurality of dispersions may be obtained by a same calculation as used to obtain the dispersion in the cumulative frequency distribution of the at least one user.

Item 9

In the skin evaluation device according to the seventh item, the reference data may indicate a previously obtained value of the dispersion in the cumulative frequency distribution of the at least one user.

Item 10

The skin evaluation device according to any one of the first to ninth items may further include a display that displays information indicating the data related to the condition of the skin.

Item 11

In the skin evaluation device according to any one of the first to tenth items, the light source may emit light as the first light, the light having a wavelength of from 650 nm to 950 nm.

Item 12

In the skin evaluation device according to the eleventh item, the light source may be a laser.

Item 13

The skin evaluation device according to any one of the first to twelfth items may further include a polarizing filter disposed between the at least one user and the image sensor, and the first light may be polarized in a specific polarization direction, and a polarization direction of light which passes through the polarizing filter may be perpendicular to the specific polarization direction.

Item 14

The skin evaluation device according to any one of the first to thirteenth items may further include a bandpass filter disposed between the at least one user and the image sensor, and a wavelength range of light which passes through the bandpass filter may include a wavelength of the first light.

Item 15

A skin evaluation system according to a fifteenth item includes: a terminal including: a light source that projects a dot pattern created by light onto a skin of a user, an image sensor that generates and outputs image data which indicates an image of the skin onto which the dot pattern is projected, and a first communication circuit that transmits characteristic data generated from the image data to an outside, the characteristic data characterizing a condition of the skin; and a server computer including: a second communication circuit that receives the characteristic data, a memory that stores reference data to evaluate the condition of the skin; and an arithmetic circuit that compares the characteristic data with the reference data to evaluate the condition of the skin of the user, and generates data related to advice for improving the condition of the skin.

Item 16

In the skin evaluation system according to the fifteenth item, the reference data may be data that characterizes a past condition of the skin of the user, and the characteristic data may be data that characterizes a current condition of the skin of the user.

Item 17

In the skin evaluation system according to the fifteenth item or the sixteenth item, the second communication circuit may transmit the data related to advice for improving the condition of the skin to the first communication circuit.

Item 18

A skin evaluation method according to an eighteenth item includes: obtaining characteristic data that characterizes a condition of a skin of a user; evaluating the condition of the skin by comparing the characteristic data with reference data recorded in a memory to evaluate the condition of the skin; and generating data related to advice for improving the condition of the skin.

Item 19

In the skin evaluation method according to the eighteenth item, the reference data may be first characteristic data that characterizes a past condition of the skin of the user, the characteristic data may be second characteristic data that characterizes a current condition of the skin of the user. The skin evaluation method may further include obtaining at least one piece of activity data related to at least one activity of the user in a period since the first characteristic data is recorded in the memory until a present time. In the evaluating the condition of the skin, change in the condition of the skin may be evaluated by comparing the first characteristic data with the second characteristic data, and first data may be determined from the at least one piece of activity data, the first data being related to the change in the condition of the skin. In the generating data related to advice for improving the condition of the skin, second data may be generated as the data related to advice for improving the condition of the skin based on the first data, the second data being related to advice suggesting to change an activity of the user, and the activity being among the at least one activity and corresponding to the first data.

Item 20

A non-transitory computer-readable recording medium according to a twentieth item is a non-transitory computer-readable recording medium storing a program causing a computer to execute a process for evaluation of a skin of a user, the process including: obtaining characteristic data that characterizes a condition of the skin of the user; evaluating the condition of the skin by comparing the characteristic data with reference data recorded in a memory to evaluate the condition of the skin; and generating data related to advice for improving the condition of the skin.

Item 21

A program according to an aspect of the present disclosure is executable by a computer for evaluation of a skin of a user, and causes a computer execute a process including: obtaining characteristic data that characterizes a condition of the skin of the user; evaluating the condition of the skin by comparing the characteristic data with reference data recorded in a memory to evaluate the condition of the skin; and generating data related to advice for improving the condition of the skin.

Each embodiment described below represents a comprehensive or specific example. Numerical values, shapes, materials, components, arrangement positions and connection configurations of the components, steps, the order of the steps shown in the following embodiment provide an example, and are not intended to limit the present disclosure. In addition, among the structural components in the subsequent embodiment, components not recited in any one of the independent claims which provide the most generic concepts are described as arbitrary structural components.

In the present disclosure, a circuit, a unit, a device, all or part of a member or a component, or all or part of a functional block of a block diagram may be executed by one or multiple electronic circuits including a semiconductor device, a semiconductor integrated circuit (IC), or a large scale integration (LSI). The LSI and IC may be integrated in one chip, or may be comprised by combining multiple chips. For instance, a functional block other than a memory device may be integrated in one chip. Here, LSI and IC are each used as a reference name, however, the reference name may be changed according to the degree of integration, and a system LSI, a very large scale integration (VLSI), or an ultra large scale integration (ULSI) may be used. A filed programmable gate array (FPGA) which is programmed after an LSI is manufactured, or a reconfigurable logic device in which a connection relationship inside an LSI is reconfigurable and circuit division inside an LSI is settable may be used for the same purpose.

In addition, a circuit, a unit, a device, a function or an operation of all or part of a member or a component may be executed by software processing. In this case, software is recorded in a non-transitory recording medium, such as one or multiple ROMS, optical discs, hard disk drives, and when the software is executed by a processing device (processor), the function identified by the software is executed by the processing device (processor) and the peripheral devices. The system and the device may include one or multiple non-transitory recording media on which software is recorded, a processing device (processor), and a hardware device needed, for instance, an interface.

Hereinafter, an embodiment will be specifically described with reference to the drawings.

Embodiment

A skin evaluation device in an embodiment of the present disclosure enables quantification of a skin condition with high accuracy. The "quantification with high accuracy" means that sensual evaluation by a person or a specialist is expressed in terms of an objective numerical value, as compared with a conventional method. The principle for evaluating skin condition will be described before the skin evaluation device is described.

FIG. 1A is an illustration for explaining the principle for evaluating skin condition. A light source 1 projects multiple discretely arranged dot images created by light onto a target object including a skin 3 of a user. In the present description, multiple dot images may be referred to as a "dot pattern". Light L0 is emitted from the light source 1. Direct reflection light L1 is reflected by a skin surface 4. Diffuse reflection light L2 enters the inside of the skin 3, and is scattered in the skin inside, then exits through the skin surface 4. A camera 2 detects the direct reflection light L1 returned from the skin 3 and at least part of the diffuse reflection light L2, and outputs a signal according to the intensity distribution of the detected light.

Figure 1B:
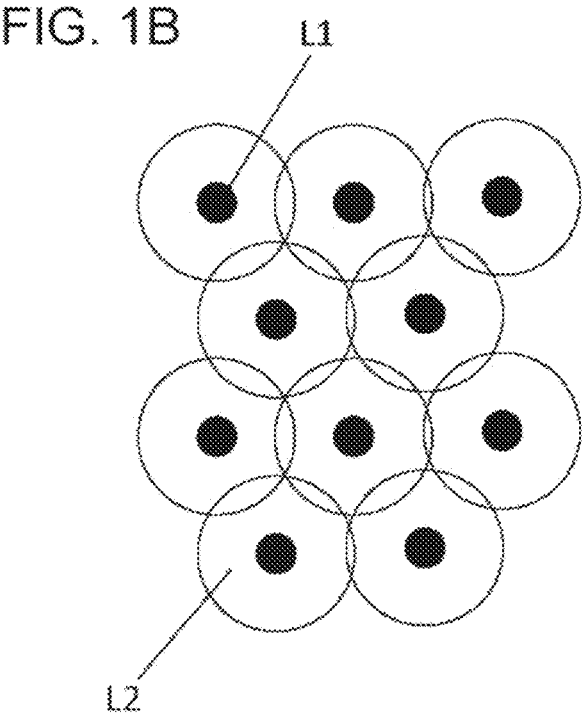
FIG. 1B is an illustration for explaining the characteristics of an image of a skin surface captured by a camera.

FIG. 1B is an illustration for explaining the characteristics of an image of the skin surface 4 captured by the camera 2. The direct reflection light L1 keeps the image of the dot pattern of the light source 1. In contrast, the diffuse reflection light L2 lost the image of the dot pattern of the light source 1 due to intense scattering within the skin. The diffuse reflection light L2 may be called the light in the surroundings of the dot pattern. The direct reflection light L1 and the diffuse reflection light L2 can be spatially separated easily by projecting a dot pattern created by light onto the skin 3.

The skin 3 illustrated in FIG. 1A contains an epidermis 33, a dermis 34, and a hypodermal tissue 35. Part of the light which has entered the inside of the skin is absorbed by the melanin pigments within the epidermis 33 and/or the hemoglobin in a blood vessel, such as a capillary 31 within the dermis 34, and an arteriovenous vessel 32. On the other hand, most of the light is intensely scattered by the collagen fiber within the dermis 34, and is emitted again through the skin surface. This is the diffuse reflection light L2. The direct reflection light L1 is reflected by the skin surface, thus is not affected by the collagen fiber inside the skin, and includes no information on the inside of the skin. The direct reflection light L1 is noise interfering with acquisition of information on the collagen fiber within the dermis 34. The direct reflection light L1 is not only useless for acquisition of internal information on the skin 3, but also prevents acquisition of accurate internal information on the skin 3. In order to detect the information on the inside of the skin with high accuracy, it is extremely important to reduce the effect of the direct reflection light L1, and acquire the information on the diffuse reflection light L2 efficiently. For instance, a polarizing filter is effective for removing the direct reflection light L1.

In the skin evaluation device in the present embodiment, the wavelength of the light from the light source 1 may be set to approximately 650 nm or greater and approximately 950 nm or less, for instance. The wavelength range is included in the wavelength range from red to near infrared. In the present description, the term "light" is used not only for visible light, but also for infrared light. The above-mentioned wavelength range is called a "biological window", and light in the range is known to have a low absorption rate in a human body.

Figure 2:
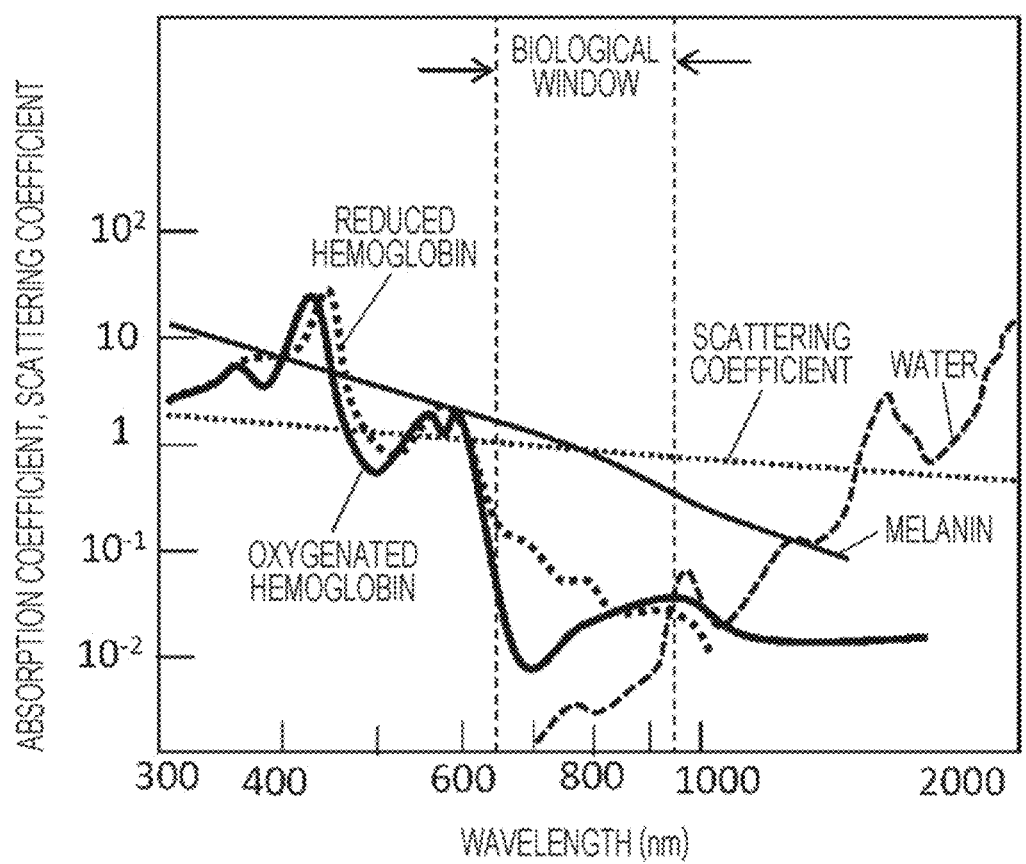
FIG. 2 is a graph illustrating the wavelength dependence of the absorption coefficient of light and the scattering coefficient of light in a human body for each of reduced hemoglobin, oxygenated hemoglobin, melanin, and water.

FIG. 2 is a graph illustrating the wavelength dependence of the absorption coefficient of light and the scattering coefficient of light in a human body for each of reduced hemoglobin, oxygenated hemoglobin, melanin, and water. In the visible light range less than or equal to 650 nm, absorption of light by blood, that is, hemoglobin is high. In contrast, in the wavelength region greater than 950 nm, absorption of light by water is high. Therefore, the light in these ranges is not suitable for acquisition of the information on the inside of the skin. However, in the wavelength range approximately 650 nm or greater and approximately 950 nm or less, the absorption coefficient of hemoglobin and water is relatively low, and the scattering coefficient thereof is relatively high. Thus, after entering the body, the light in the wavelength range is intensely scattered and returned to the body surface. Consequently, it is possible to acquire the information on a deep part of the skin efficiently.

In the skin evaluation device in the present embodiment, the light in the wavelength region corresponding to the "biological window" is primarily used, which is the wavelength range approximately 650 nm or greater and approximately 950 nm or less.

Hereinafter, the skin evaluation device in the present embodiment will be specifically described with reference to FIGS. 3A and 3B.

Figure 3A:
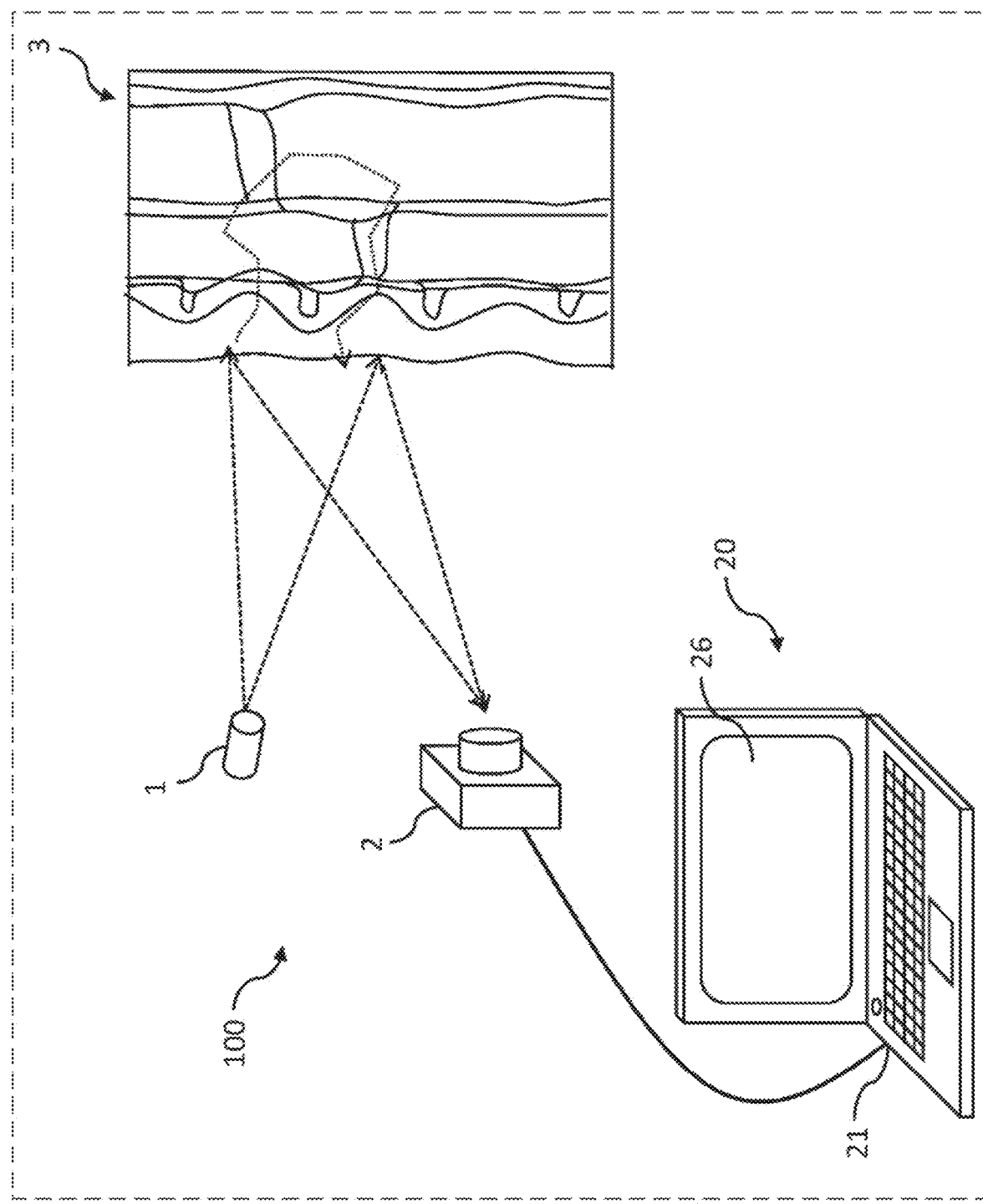
FIG. 3A is an illustration schematically showing an example of an evaluation device in the present embodiment.

FIG. 3A is an illustration schematically showing an example of a skin evaluation device 100 in the present embodiment. The skin evaluation device 100 in the present embodiment includes the light source 1, the camera 2, and a computer 20.

The light source 1 projects a dot pattern created by light onto the skin 3 of a user. The light source 1 is disposed at a position away from the skin 3. The light source 1 emits light in the wavelength region of near infrared. The light source 1 is designed to project a dot pattern onto the skin surface 4. The dot pattern is typically a set of fine bright spots arranged two-dimensionally. A one-dimensionally arranged dot pattern may be used depending on application. In the skin evaluation device 100 in the present embodiment, a random dot pattern laser projector RPP017ES manufactured by Osela Inc. in the U.S. is used as the light source 1. The laser light source emits near infrared light of 830 nm. The laser light source projects a dot pattern including 57466 points in a view angle of 45°×45°. For projection of a dot pattern, a dot pattern laser projector comprised of laser light and a diffraction optical device is used. Use of laser light as the light source 1 enables projection of a dot pattern onto the skin 3 without focus blur even when the distance between the skin 3 and the camera 2 is changed. Conventional pattern projection using a diffraction optical system has a problem in that focus blur of a projected pattern caused by variation in the distance reduces the measurement accuracy significantly. To avoid the problem, conventionally, an illumination optical system is strictly adjusted before measurement. Another advantage of laser light is that the laser light has polarization characteristics. Using both of a laser light source and a polarizing filter makes it possible to remove most of the component of the direct reflection light L1 easily.

Figure 3B:
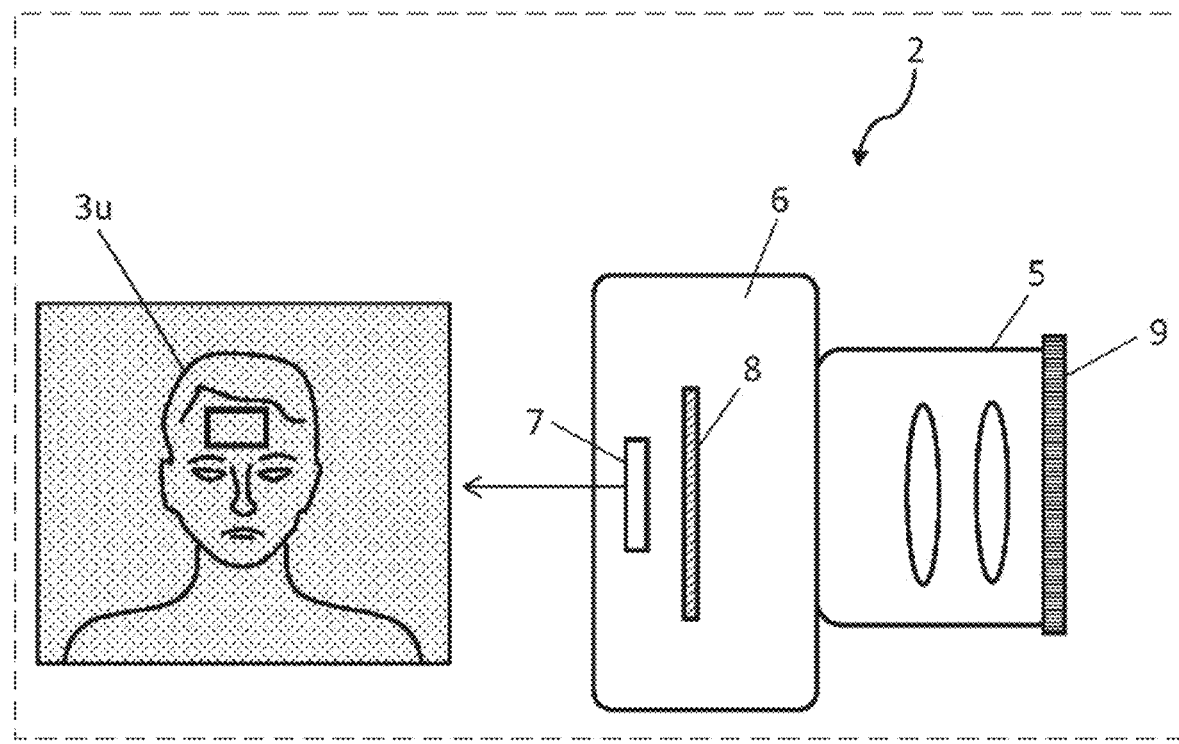
FIG. 3B is an illustration showing an example of a configuration of a camera and an image of a user.

FIG. 3B is an illustration showing an example of a configuration of the camera 2 and an image of a user 3u. The camera 2 includes a lens 5 and a housing 6. The lens 5 may be a set of multiple lenses. The lens 5 is disposed in front of the housing 6. It may be stated that the lens 5 is disposed between the housing 6 and the user 3u which is not illustrated. The inside of the housing 6 is provided with an image sensor 7 and a bandpass filter 8. The image sensor 7 obtains an image of the user 3u, on which a dot pattern is projected. The image sensor 7 generates and outputs image data indicating the image of the user 3u. The left side of FIG. 3B shows the image of the user 3u obtained from the image data. The image includes the dot pattern. The dot pattern has a pixel value according to the reflection rate of near infrared light at each position. The higher the reflection rate, the greater the pixel value. In the example illustrated in FIG. 3B, the bandpass filter 8 is disposed between the lens 5 and the image sensor 7. It may be stated that the bandpass filter 8 is disposed between the user 3u (not illustrated) and the image sensor 7. Only the light having a wavelength of 830 nm (the wavelength of the light source 1)±10 nm passes through the bandpass filter 8. In other words, the wavelength range of light which passes through the bandpass filter 8 includes the wavelength of light emitted from the light source 1.

In the skin evaluation device 100 in the present embodiment, a semiconductor laser light source is used as the light source 1. The laser light has linear polarization characteristics. Thus, a polarizing filter does not need to be disposed at the light source 1. In the example illustrated in FIG. 3B, a polarizing filter 9 is disposed in front of the lens 5. It may be stated that the polarizing filter 9 is disposed between the user 3u (not illustrated) and the image sensor 7. The polarizing filter 9 is disposed in a direction perpendicular to the polarization direction of the light source 1. This is so-called cross Nicol arrangement. In other words, the polarization direction of light passing through the polarizing filter 9 is perpendicular to the specific polarization direction of light projected onto the user 3u. Capturing an image by the camera 2 through the polarizing filter 9 can reduce the effect of the direct reflection light L1. It is possible to obtain the information on the inside of the skin with high accuracy by removing most of the component of the direct reflection light L1 with the polarizing filter 9.

Figure 3C:
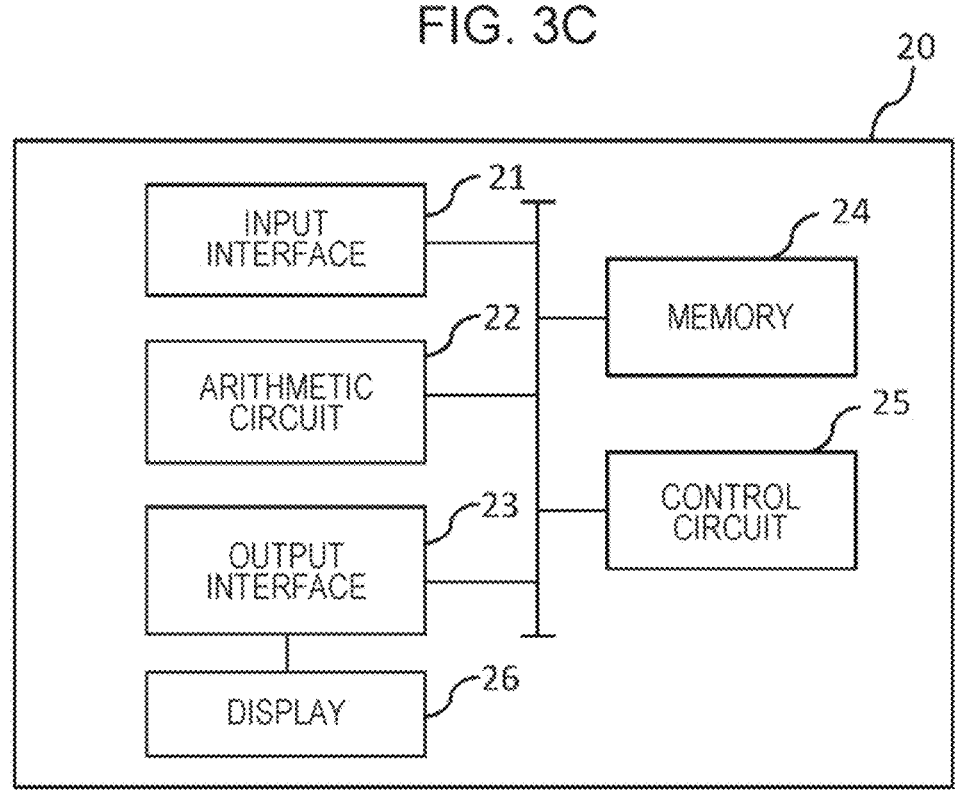
FIG. 3C is a block diagram schematically illustrating the configuration of a computer.

FIG. 3C is a block diagram schematically illustrating the configuration of the computer 20. The computer 20 includes an input interface 21, an arithmetic circuit 22, a memory 24, a control circuit 25, an output interface 23, and a display 26. The camera 2 and the input interface 21 are electrically connected. Image data outputted from the image sensor 7 is inputted to the input interface 21. The memory 24 is a recording medium that records reference data for evaluating the condition of the skin 3. The arithmetic circuit 22 obtains image data from the input interface 21, and reference data from the memory 24. The arithmetic circuit 22 generates and outputs data related to the condition of the skin 3 based on the image data and the reference data. Specific processing of the arithmetic circuit 22 will be described later. The control circuit 25 controls the entire operation of the computer 20. The output interface 23 outputs data. The output interface 23 and the display 26 are electrically connected. The display 26 displays a processing result indicated by the data outputted from the output interface 23.

The arithmetic circuit 22 may be an image processing circuit, such as a digital signal processor (DSP). The control circuit 25 may be an integrated circuit, such as a central processing unit (CPU) or a microcomputer. The control circuit 25 executes a control program recorded, for instance, in the memory 24, and controls the lighting of the source light 1, image capturing of the camera 2, and the calculation of the arithmetic circuit 22. The arithmetic circuit 22 and the control circuit 25 may be implemented by one integrated circuit. In the example illustrated in FIG. 3C, the computer 20 includes the display 26. However, the display 26 may be an external device which is electrically connected via a wire or wirelessly. The computer 20 may obtain image data from the camera 2 at a remote place via a communication line which is not illustrated.

Hereinafter, an example of a method of evaluating the condition of the skin 3 using actually measured data will be described.

Figure 4A:
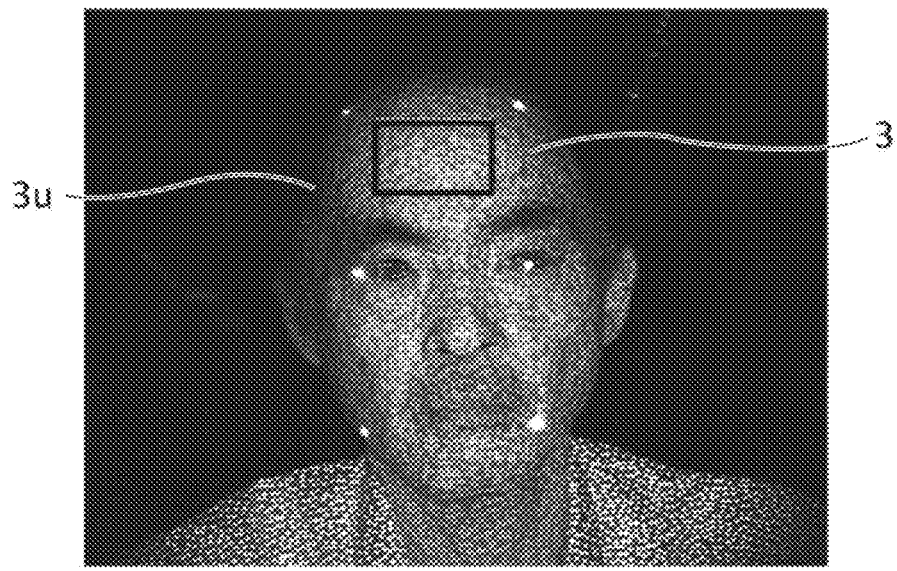
FIG. 4A is a photograph illustrating an example of an image captured by a camera.

FIG. 4A is a photograph illustrating an example of an image of the user 3u captured by the camera 2. The camera 2 is a near infrared light camera. In the skin evaluation device 100 in the present embodiment, most of the component of the direct reflection light L1 is removed by the polarizing filter 9, however, the component is not completely removed. Thus, as illustrated in FIG. 4A, a dot pattern caused by the direct reflection light L1 is observed in the obtained image. A clear dot pattern is observed in a portion of clothes where the rate of the direct reflection light L1 is high. In contrast, in the skin 3, irradiation light enters the inside and is diffusely reflected. Thus, the contrast of the dot pattern is reduced as compared with the clothes.

Figure 4B:
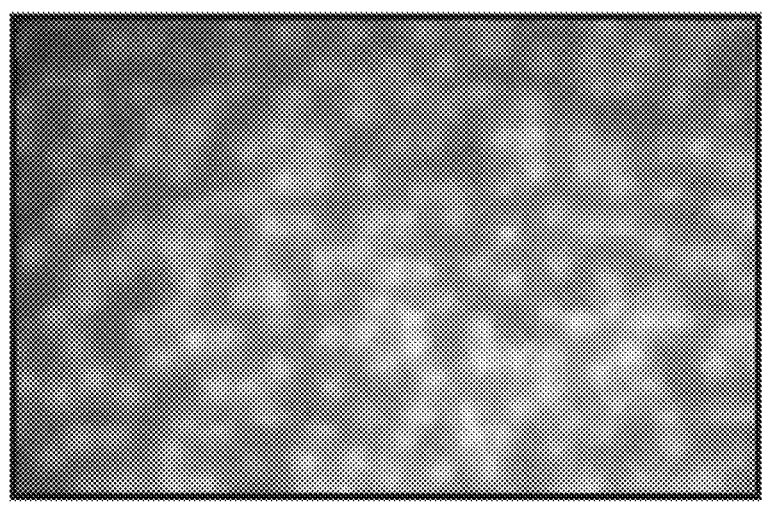
FIG. 4B is an enlarged view of a target area surrounded by a thick line illustrated in FIG. 4A.

FIG. 4B is an enlarged view of a target area surrounded by a thick line illustrated in FIG. 4A. The target area is a forehead area. As illustrated in FIG. 4B, a dot pattern created by light can be identified even in a skin area.

Figure 4C:
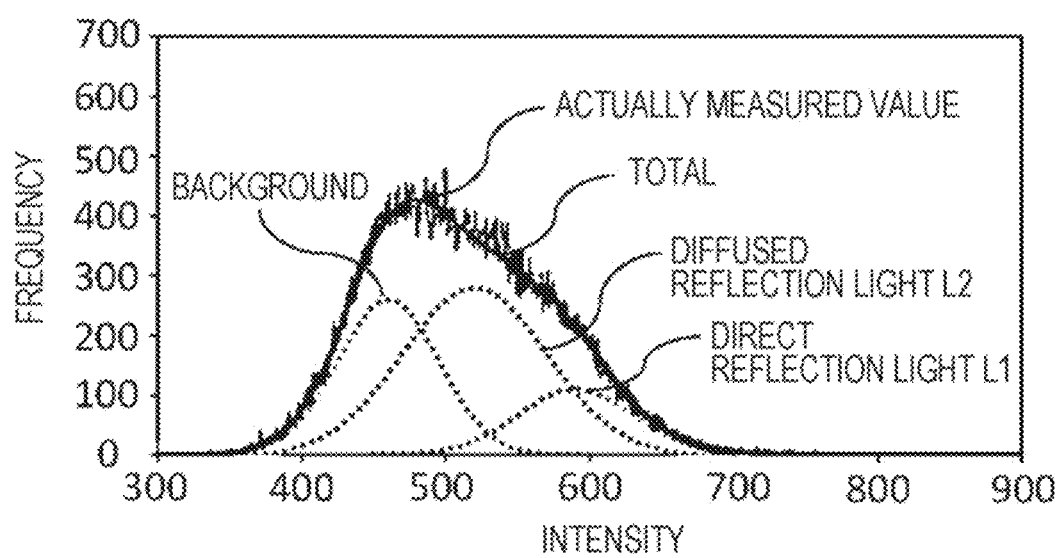
FIG. 4C is a graph illustrating actually measured values and calculated values of the frequency distribution generated from the image illustrated in FIG. 4B.

FIG. 4C is a graph illustrating actually measured values and calculated values of the frequency distribution generated from the image illustrated in FIG. 4B. The horizontal axis indicates the intensity of light received by pixels. The intensity is expressed by a pixel value which is at most a 10 bit integer, that is, $2^{10}=1024$. The vertical axis indicates a frequency of the intensity. The frequency corresponds to the number of pixels each having the pixel value. The significantly oscillating curve represents actually measured values. The actually measured values include random noise. The component of the direct reflection light L1, the component of the diffuse reflection light L2, and the component of the background are separated as the calculated values from the actually measured values.

Under the assumption that each component of the direct reflection light L1, the diffuse reflection light L2, and the background follows a gaussian distribution, the arithmetic circuit 22 fits the actually measured values with three gaussian distributions. It is probable that between the three gaussian distributions, the gaussian distribution having the largest average value is the component of the direct reflection light L1, the gaussian distribution having the second largest average value is the component of the diffuse reflection light L2, and the gaussian distribution having the least average value is the component of the background. The component of the background is probably the reflection component of light other than the light for a dot pattern. This is because although small in amount, light other than the light for a dot pattern is emitted from the light source 1.

The component of the direct reflection light L1 within the epidermis 33 is expressed by $g_1(x)=A_1 \exp\{-(x-\mu_1)^2/(2\sigma_1^2)\}$. The component of the diffuse reflection light L2 within the dermis 34 is expressed by $g_2(x)=A_2 \exp\{-(x-\mu_2)^2/(2\sigma_2^2)\}$. The component of the background is expressed by $g_3(x)=A_3 \exp\{-(x-\mu_3)^2/(2\sigma_3^2)\}$. $A_1$ to $A_3$ are peak heights, $\mu_1$ to $\mu_3$ are average values and satisfy $\mu_1>\mu_2>\mu_3$. $\sigma_1$ to $\sigma_3$ are standard deviations. For fitting of actually measured values, the difference between the actually measured values of frequency distribution and $f(x)=g_1(x)+g_2(x)+g_3(x)$ is repeatedly calculated by changing each parameter. Thus, nine parameters $(A_1, \mu_1, \sigma_1)$, $(A_2, \mu_2, \sigma_2)$, $(A_3, \mu_3, \sigma_3)$ that minimize the difference are determined. For instance, when the sum of the squares of the error between the actually measured value of frequency distribution at each intensity and $f(x)$ is minimized, the difference is determined to be the minimum.

As illustrated in FIG. 4C, it is seen that the sum of the three gaussian distributions determined by the fitting match the actually measured values very well. It is seen that the component of the direct reflection light L1 and the component of the diffuse reflection light L2 are separated from the frequency distribution. The component of the diffuse reflection light L2 reflects the degree of scattering within the dermis 34. The degree of scattering represents the property of beautiful skin. Thus, the condition of the skin 3 can be evaluated from the component of the diffuse reflection light L2.

Figure 5A:
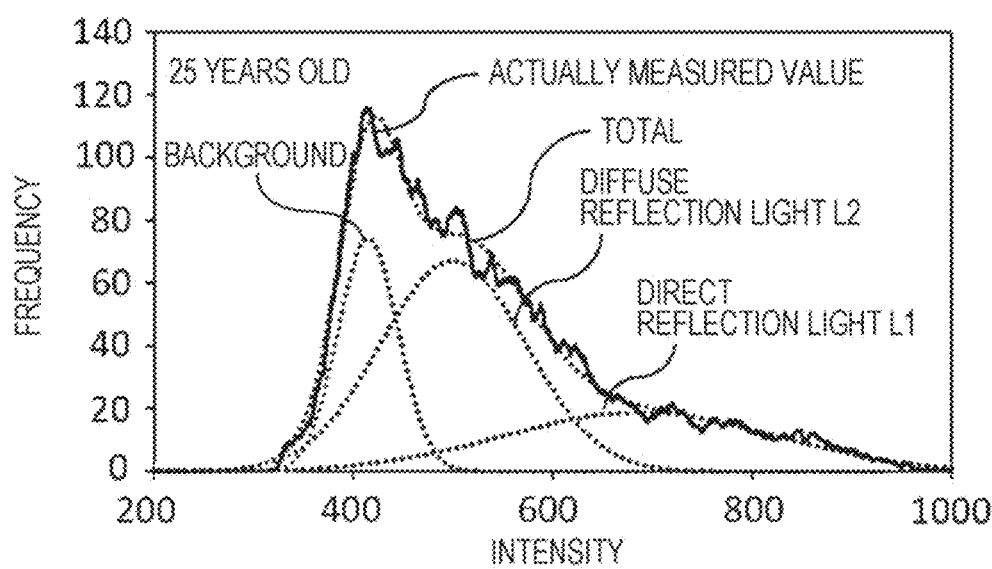
FIG. 5A is a graph illustrating actually measured values and calculated values of the frequency distribution obtained from a user at the age of 25.
Figure 5B:
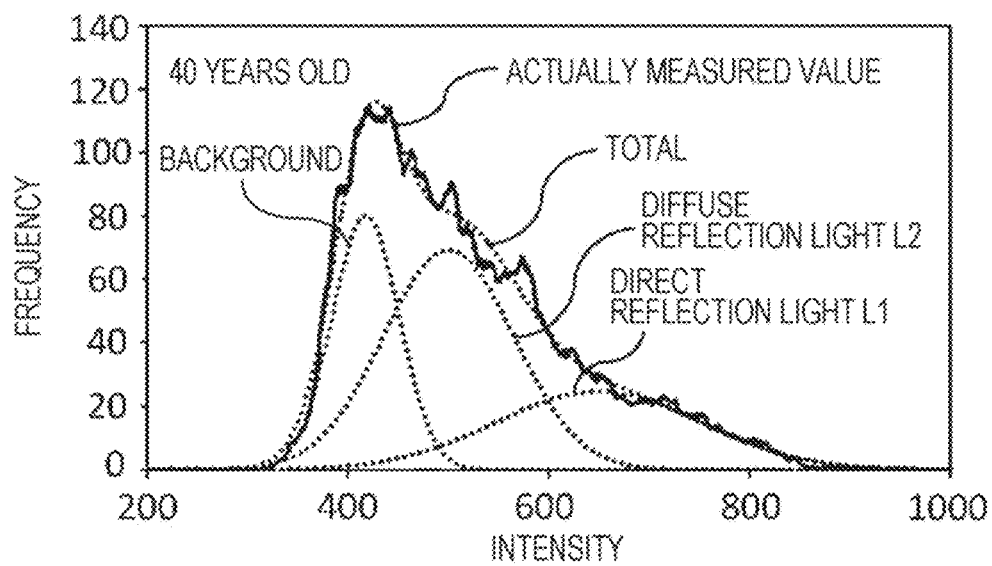
FIG. 5B is a graph illustrating actually measured values and calculated values of the frequency distribution obtained from a user at the age of 40.
Figure 5C:
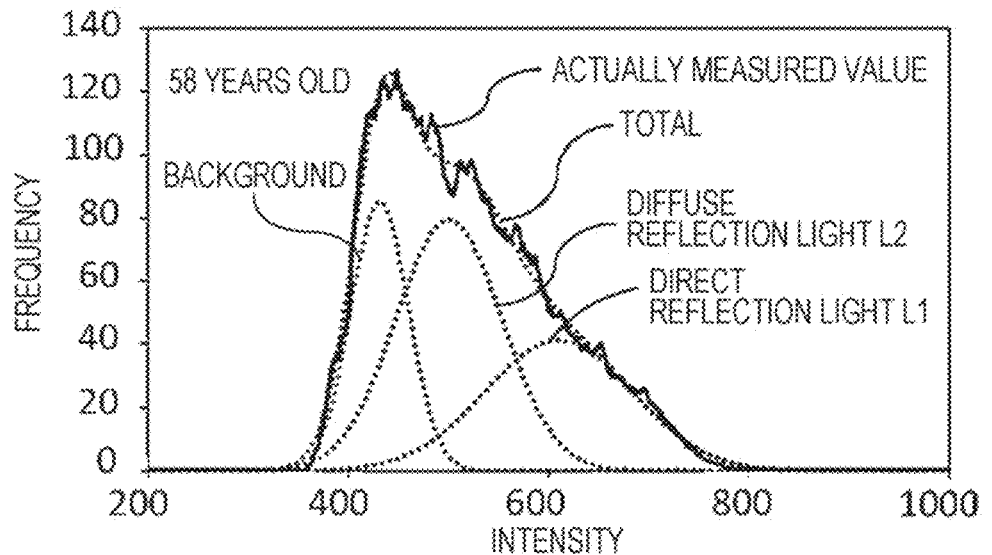
FIG. 5C is a graph illustrating actually measured values and calculated values of the frequency distribution obtained from a user at the age of 58.

FIGS. 5A to 5C are graphs illustrating actually measured values and calculated values which are obtained from the frequency distributions of users at the age of 25, 40, and 58. By the above-described fitting, the component of the direct reflection light L1, the component of the diffuse reflection light L2, and the component of the background are separated from the actually measured values of each frequency distribution. At first glance, the difference between the actually measured values of the three frequency distributions is not clear. However, for instance, the gaussian distribution located at the center, showing the component of the diffuse reflection light L2, has a shape which is different user by user.

Figure 6:
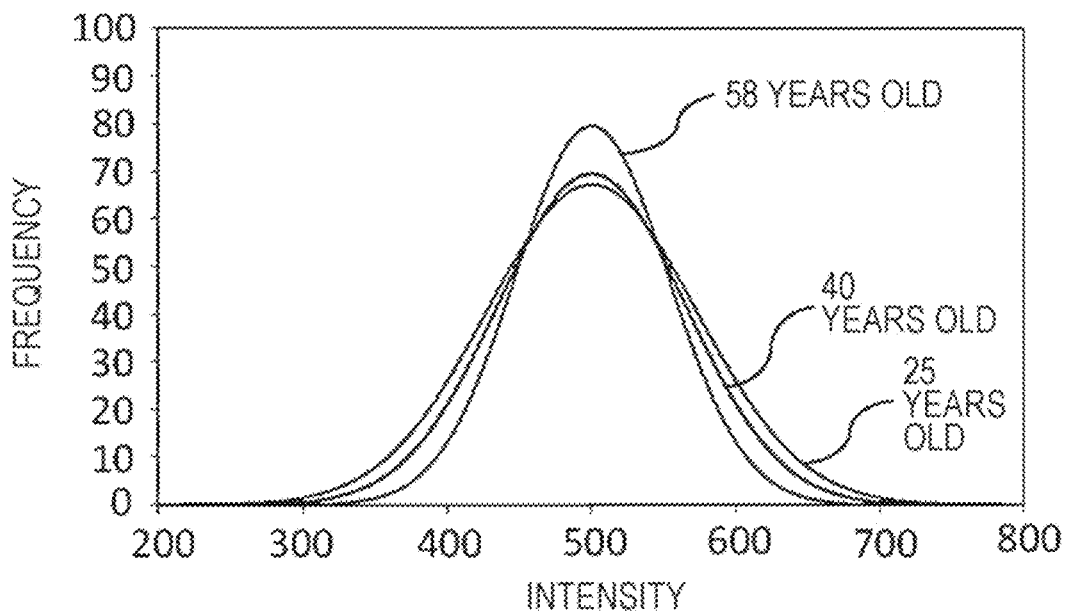
FIG. 6 is a graph illustrating the components of the diffuse reflection light obtained from the users at the ages of 25, 40 and 58.

FIG. 6 is a graph illustrating the component of the diffuse reflection light L2 obtained from the users at the ages of 25, 40 and 58. The average values of intensity are substantially the same regardless of the age. However, the width of each gaussian distribution is smaller for older age. This means that the older the age, the lower the degree of diffuse reflection, that is, the scattering coefficient.

Figure 7:
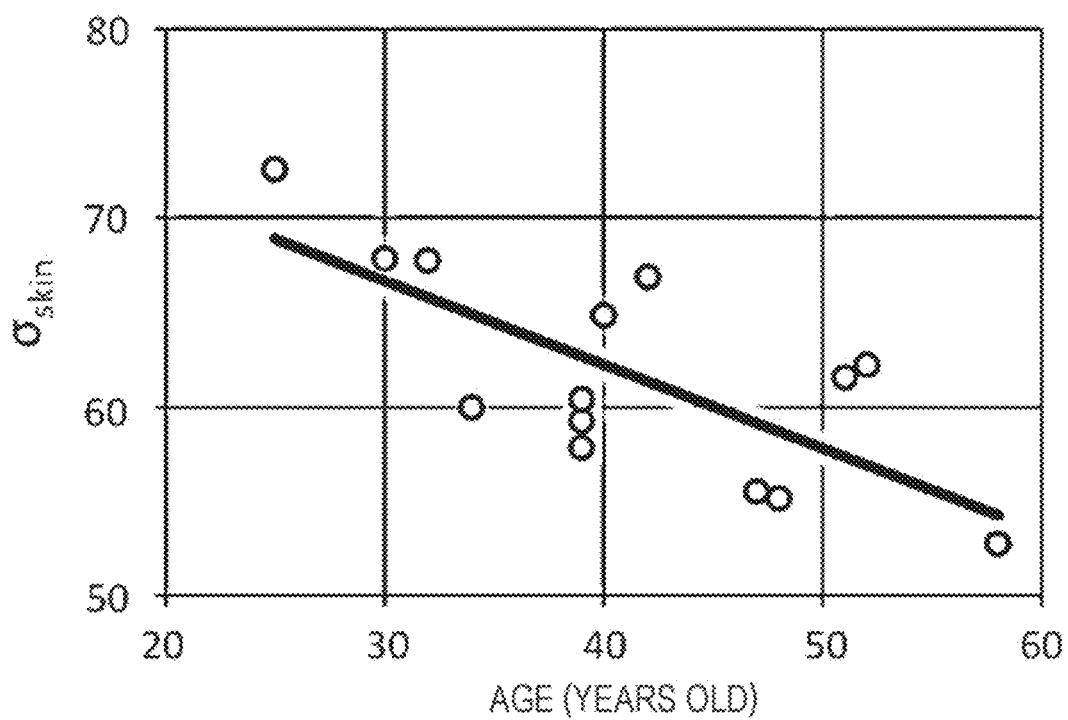
FIG. 7 is a graph illustrating the relationship between age and standard deviation of the component of the diffuse reflection light.

FIG. 7 is a graph illustrating the relationship between age and standard deviation $\sigma_{skin}$ of the component of the diffuse reflection light L2. The open circles indicate the standard deviations obtained from 14 users at the age from 25 to 58. The straight line indicates a linear function calculated from the multiple open circles by the least square method. It is seen from the linear function that although there is a difference among individuals, the standard deviation of the component of the diffuse reflection light L2 tends to be lower for older age. Collagen is produced by fibroblast cells. It is known that the amount of collagen within the dermis 34 is reduced by functional deterioration of fibroblast cells due to aging. Some data shows that the amount of collagen in one's sixties is only 30% of that in one's twenties. Based on such data, aging of the skin 3 is probably caused by reduction in the amount of collagen. As described above, light scattering by the collagen fiber within the dermis 34 determines diffuse reflection in the skin. The collagen condition of the skin 3 can be estimated by measuring the component of the diffuse reflection light L2 of the skin 3 with the skin evaluation device 100 in the present embodiment. For instance, the skin age is given by an age which is obtained by comparison between the linear function illustrated in FIG. 7 and the standard deviation calculated from the component of the diffuse reflection light L2.

It is known that the amount of collagen of the skin 3 is affected not only by age, but also by ultraviolet rays, high blood glucose, and an eating habit problem such as amino acid, vitamin C insufficiency. The collagen condition of the skin 3 can be estimated in daily life by the skin evaluation device 100 in the present embodiment. This allows attention to be paid to daily life according to the condition of the skin 3. Consequently, it is expected that beautiful skin can be maintained.

Figure 8:
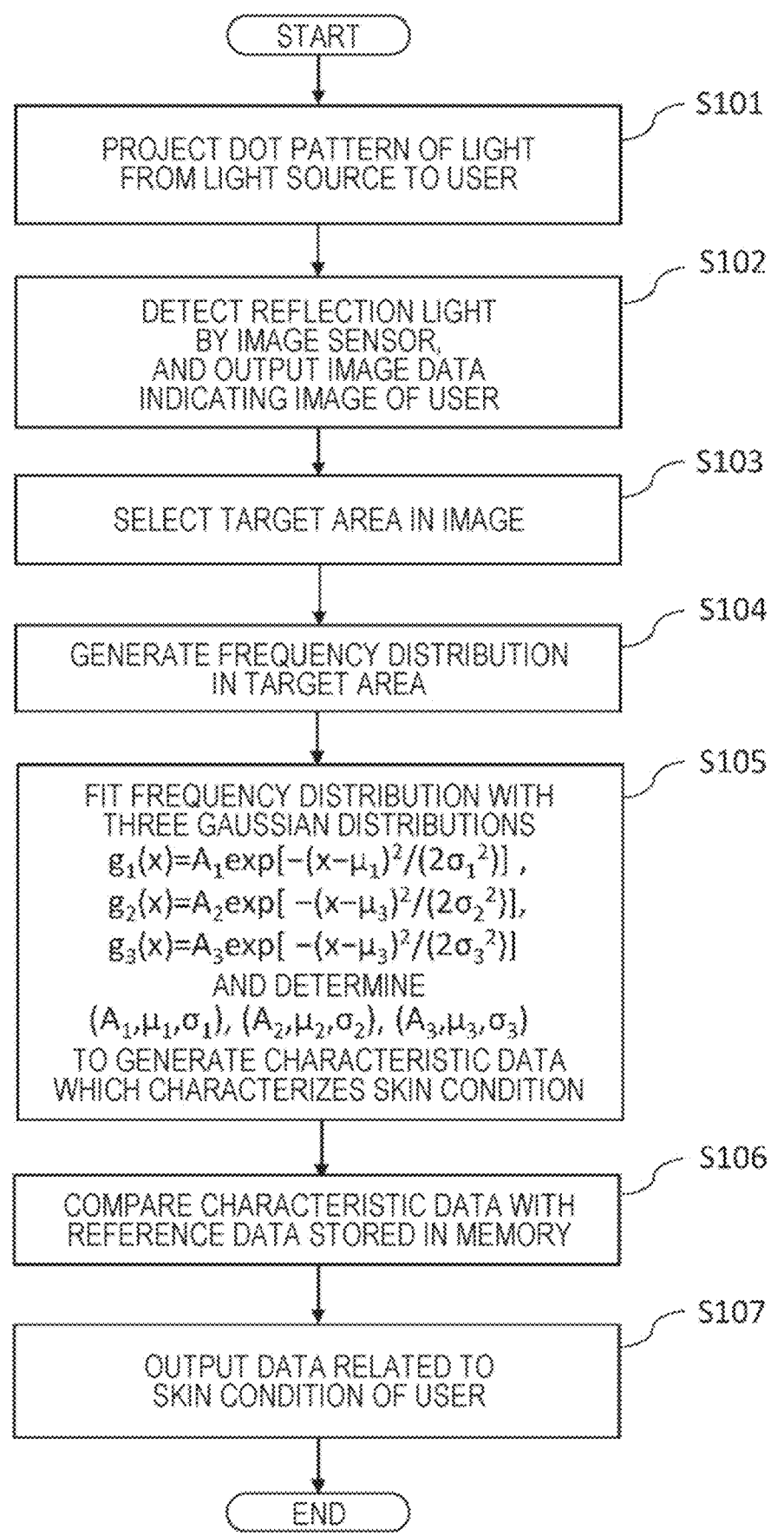
FIG. 8 is a flowchart illustrating the operation of a skin evaluation device in the present embodiment.

FIG. 8 is a flowchart illustrating the operation of the skin evaluation device 100 in the present embodiment.

In step S101, a dot pattern created by light is projected from the light source 1 onto the skin 3 of the user 3u. The light source 1 is, for instance, a laser light source. In this case, the light projected onto the skin 3 of the user 3u is polarized in a specific direction.

In step S102, the reflection light from the user 3u is detected by the image sensor 7, and image data indicating the image of the user 3u is outputted. When the light source 1 is a laser light source, most of the component of the direct reflection light L1 out of the reflection light from the user 3u is removed by the polarizing filter 9. The outputted image data is inputted from the image sensor 7 to the input interface 21 wirelessly or via a wire.

In step S103, the arithmetic circuit 22 selects at least a partial area in the image as a target area. The target area is, for instance, a forehead area of the user 3u. The target area may be a nose area, a cheek area, or a jaw area of the user 3u.

In step S104, from the image data, the arithmetic circuit 22 generates a frequency distribution showing the relationship between intensity and the frequency of the intensity in the target area. The frequency distribution includes the component of the direct reflection light L1, the component of the diffuse reflection light L2, and the component of the background. These three components are separated from the frequency distribution in the next step.

In step S105, the arithmetic circuit 22 fits the frequency distribution with the above-mentioned three gaussian distributions $g_1(x)$, $g_2(x)$, $g_3(x)$ to determine $(A_1, \mu_1, \sigma_1)$, $(A_2, \mu_2, \sigma_2)$, $(A_3, \mu_3, \sigma_3)$, and generates characteristic data that characterizes the condition of the skin 3. In other words, the arithmetic circuit 22 generates characteristic data that characterizes the condition of the skin 3 from the relationship between the intensity and the frequency in at least a partial area in the image indicated by the image data. The characteristic data indicates, for instance, the standard deviation $\sigma_2$ of the component of the diffuse reflection light L2. The standard deviation $\sigma_2$ of the component of the diffuse reflection light L2 reflects the beauty and youth of the skin.

In step S106, the arithmetic circuit 22 compares the characteristic data with the reference data recorded in the memory 24. The reference data shows, for instance, the values of multiple standard deviations respectively obtained from multiple users illustrated in FIG. 7. The multiple standard deviations are each obtained by the same arithmetic as used to obtain the standard deviation of the user 3u. The arithmetic circuit 22 can calculate a skin age from the linear function illustrated in FIG. 7 and the standard deviation of the component of the diffuse reflection light L2, for instance.

In step S107, the arithmetic circuit 22 outputs data related to the condition of the skin 3 of the user 3u. The display 26 displays information indicating the data related to the condition of the skin 3. The information is, for instance, a skin age.

In the embodiment described above, a small-sized and inexpensive skin evaluation device 100, which enables easy evaluation of the condition of the skin 3 in daily life, has been presented. As another embodiment, a simpler skin evaluation system will be described.

In recent years, a model of mobile phone, such as smartphone, has been released, which is provided with a light source that projects a dot array of near infrared light and a camera using near infrared light for biometric identity authentication. The model has a 3D face authentication function. By the 3D face authentication function, identity authentication is performed with high accuracy by measuring the contour of the face of the user 3u as a three-dimensional image. Although the purpose of use is different from that of the present disclosure, the same hardware is used, which projects a dot array of near infrared light onto the face of the user 3u and captures a near infrared image. Thus, the inventor has investigated whether it is possible to evaluate the condition of the skin 3 by such a mobile terminal.

Figure 9:
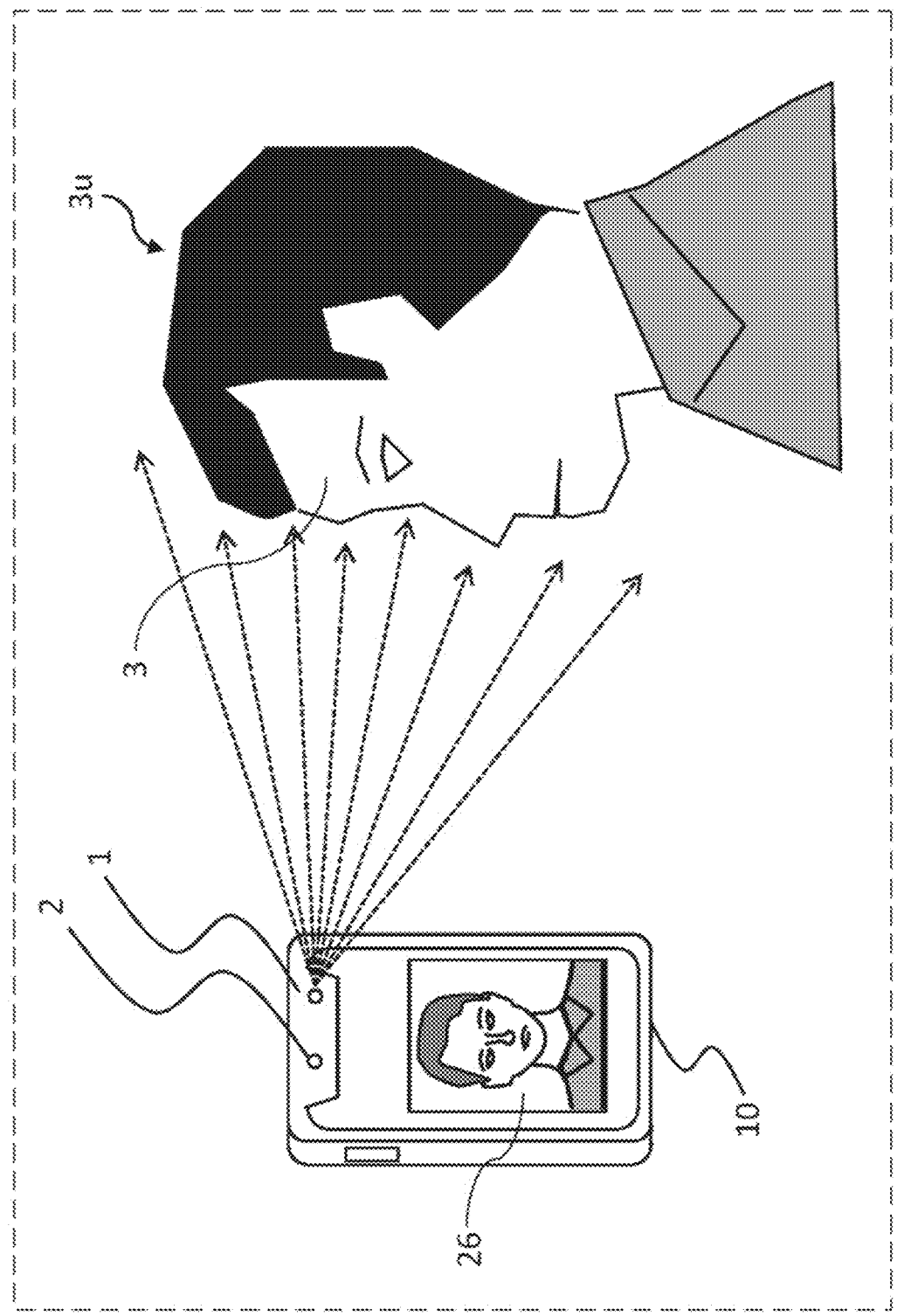
FIG. 9 is an illustration schematically showing the manner in which the skin of a user is evaluated by a mobile terminal.

FIG. 9 is an illustration schematically showing the manner in which the skin 3 of the user 3u is evaluated by a mobile terminal 10. The mobile terminal 10 is iPhone (registered trademark) X having the above-mentioned 3D face authentication function, manufactured by Apple Inc. In the iPhone (registered trademark) X, the light source 1 which projects a dot array of near infrared light with a wavelength of 940 nm, and the camera 2 using near infrared light are mounted on an upper portion. By using the mobile terminal 10, the face of the user 3u is captured by the camera 2 with the light source 1 turned on.

Figure 10:
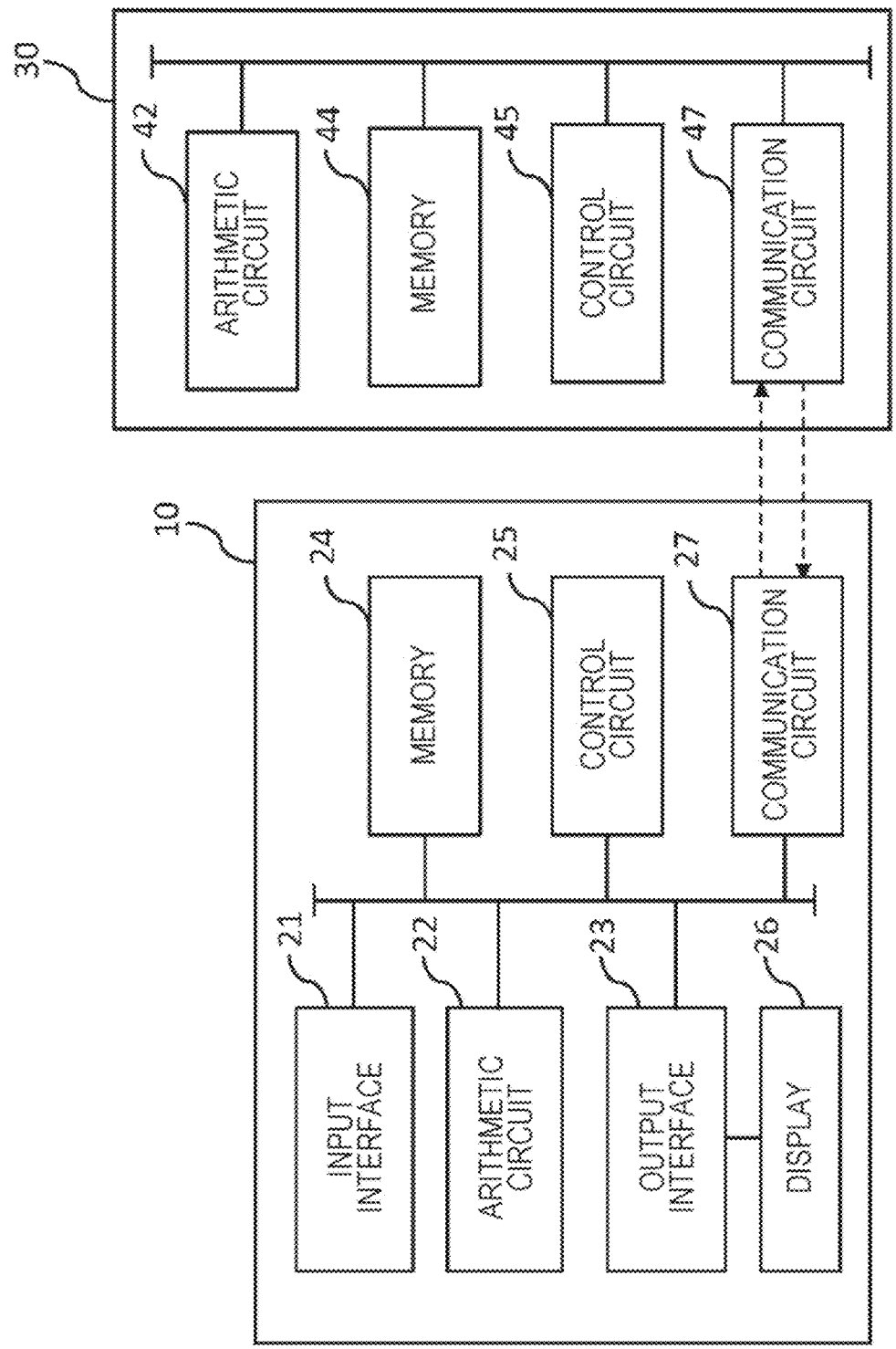
FIG. 10 is a block diagram schematically illustrating a skin evaluation system in the present embodiment.

FIG. 10 is a block diagram schematically illustrating the configuration of a skin evaluation system 200 in the present embodiment. The skin evaluation system 200 in the present embodiment includes the mobile terminal 10, and a server computer 30.

The mobile terminal 10 includes a light source 1 (not illustrated), a camera 2 (not illustrated), an input interface 21, an arithmetic circuit 22, a memory 24, a control circuit 25, an output interface 23, a display 26, and a communication circuit 27. The configuration of the mobile terminal 10 illustrated in FIG. 10 is the same as the configuration of the computer 20 illustrated in FIG. 3C except for the communication circuit 27. The arithmetic circuit 22 generates data indicating the relationship between intensity and a frequency of the intensity. The communication circuit 27 transmits the data generated by the arithmetic circuit 22 to a communication circuit 47 in the server computer 30 via wireless communication.

The server computer 30 includes an arithmetic circuit 42, a memory 44, a control circuit 45, and a communication circuit 47. The memory 44 records various types of data transmitted from the mobile terminal 10 to the server computer 30. The memory 44 also records past data of the user 3u, measured so far. The control circuit 45 controls the entire operation of the server computer 30.

For evaluation of the condition of the skin 3, the mobile terminal 10 and the server computer 30 may share the arithmetic processing. Respective pieces of the arithmetic processing to be performed by the arithmetic circuits 22, 42 are determined by the ability of the arithmetic circuits 22, 42 and the capacities of the memories 22, 44. In the skin evaluation system 200 in the present embodiment, the current condition of the skin 3 is measured by the mobile terminal 10, the measured current condition of the skin 3 is evaluated by the server computer 30, and a result of the evaluation is displayed by the mobile terminal 10. As might be expected, measurement and evaluation of the current condition of the skin 3 and display of a result of the evaluation may be performed by the mobile terminal 10 only. In this case, there is an advantage in that the mobile terminal 10 can be used standalone even in an environment of adverse wireless communication conditions.

The arithmetic circuit 42 in the server computer 30 compares the current data with the past data, and calculates an amount of change in both data. The arithmetic circuit 42 generates data related to advice for daily life based on a result of the calculation, the advice being considered to be appropriate for improving the condition of the skin 3. The advice for daily life is related to protection of ultraviolet rays, sleep, or nutrition to be taken. The communication circuit 47 transmits the data related to advice to the communication circuit 27 in the mobile terminal 10.

The mobile terminal 10 separately obtains activity data of the user 3u, such as daily sleep time, nutrient intake and/or the amount of exposure to ultraviolet rays of the user 3u. The sleep time is obtained through input of a daily sleep time by the user 3u. The nutrient intake is estimated by each meal plan inputted by the user 3u. The amount of exposure to ultraviolet rays is estimated by the outdoor activity time on a day inputted by the user 3u and the amount of ultraviolet rays on the day obtained from weather information. The communication circuit 27 in the mobile terminal 10 transmits these pieces of data obtained daily, and the data of the skin 3 of the user 3u to the communication circuit 47 in the server computer 30.

The arithmetic circuit 42 in the server computer 30 monitors daily change in the condition of the skin 3 of the user 3u, and correlation with the activity data, thereby identifying the factor of the change in the condition of the skin 3 of the user 3u. The arithmetic circuit 42 generates data related to appropriate advice to the user 3u according to the factor. For instance, when the sleep time is reduced during a period in which the degree of diffuse reflection within the dermis 34 decreases, data related to advice suggesting to have sufficient sleep is generated. When the intake of a specific nutrition such as Vitamin C in a period is lower than or equal to a reference value, data related to advice of a meal plan for intake of the nutrition is generated. When the amount of exposure to ultraviolet rays is higher than or equal to a reference value in a period, data related to advice suggesting to take ultraviolet rays measures is generated. The communication circuit 47 in the server computer 30 transmits data related to the advice to the communication circuit 27 in the mobile terminal 10.

The skin evaluation system 200 in the present embodiment enables the condition of the skin 3 to be regularly evaluated easily by the mobile terminal 10, such as a smartphone, which is carried and used daily. The condition of the skin 3 can be evaluated in a short spare time without using a special device. Even in daily life, the condition of the skin 3 can be easily evaluated, and the relevant data can be analyzed on the server computer 30. Thus, it is possible to find an effective method to improve the condition of the skin 3 for each individual, and give an appropriate advice to the individual. An individual activity habit and a condition of the skin 3 can be associated with each other by storing individual activity data and data of the condition of the skin 3 in the server computer 30. It is possible to effectively improve the condition of the skin 3 by such analysis of big data.

Figure 11:
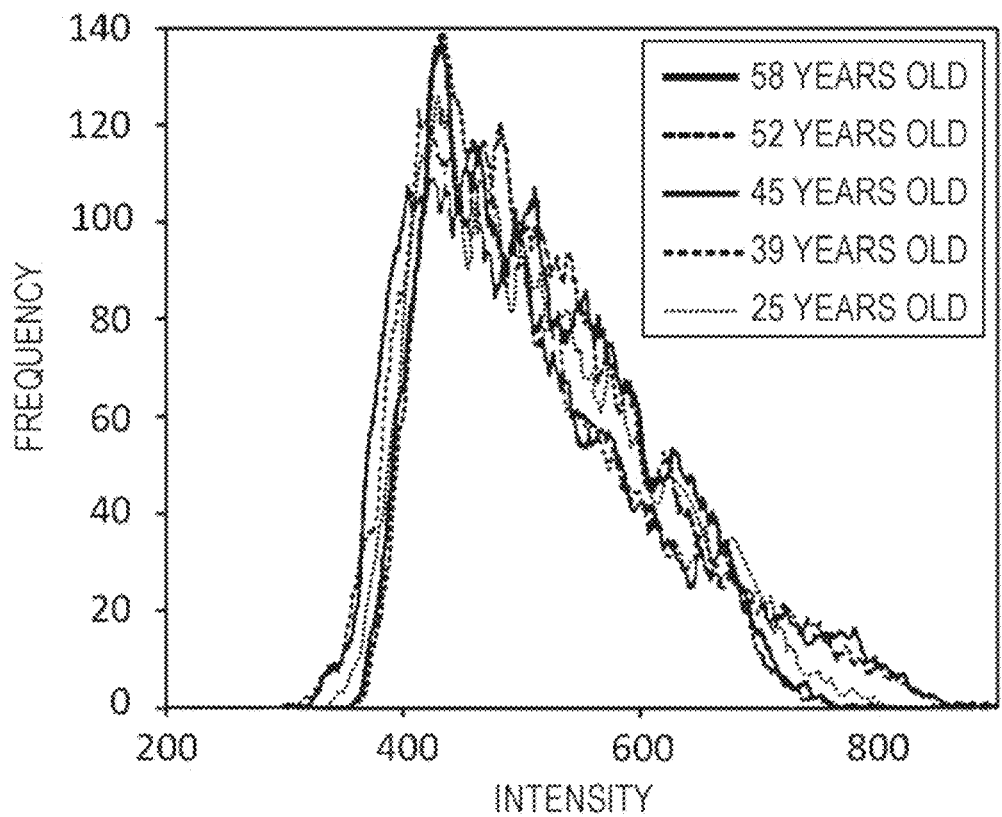
FIG. 11 is a graph illustrating the frequency distributions obtained from five users at the age from 25 to 58.
Figure 12:
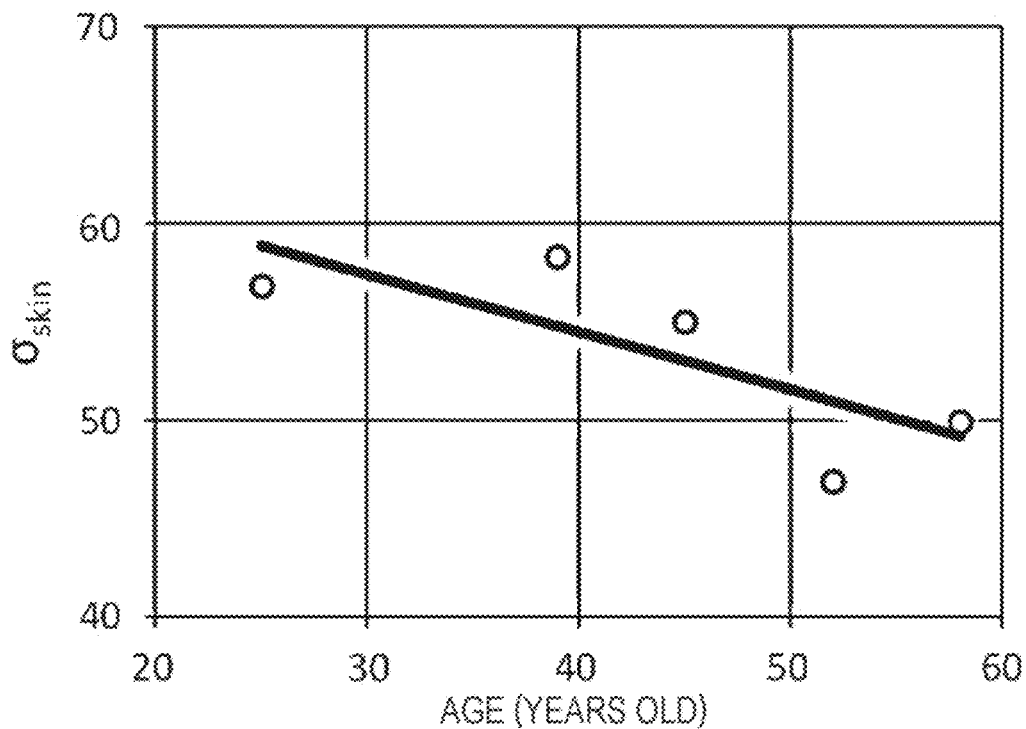
FIG. 12 is a graph illustrating the relationship between age and standard deviation of the component of the diffuse reflection light.

FIG. 11 is a graph illustrating the frequency distribution obtained from five users at the age from 25 to 58. FIG. 12 is a graph illustrating the relationship between age and standard deviation $\sigma_{skin}$ of the component of the diffuse reflection light L2. The open circles indicate the standard deviations obtained from five users. The straight line indicates a linear function calculated from the multiple open circles by the least square method. The calculation method for standard deviation is as described above. As illustrated in FIG. 12, it is seen that a clear relationship between age and diffuse reflection within the dermis 34 is obtained from the skin evaluation system 200 in the present embodiment. Thus, the effectiveness of the skin evaluation system 200 in the present embodiment has been verified.

Figure 13:
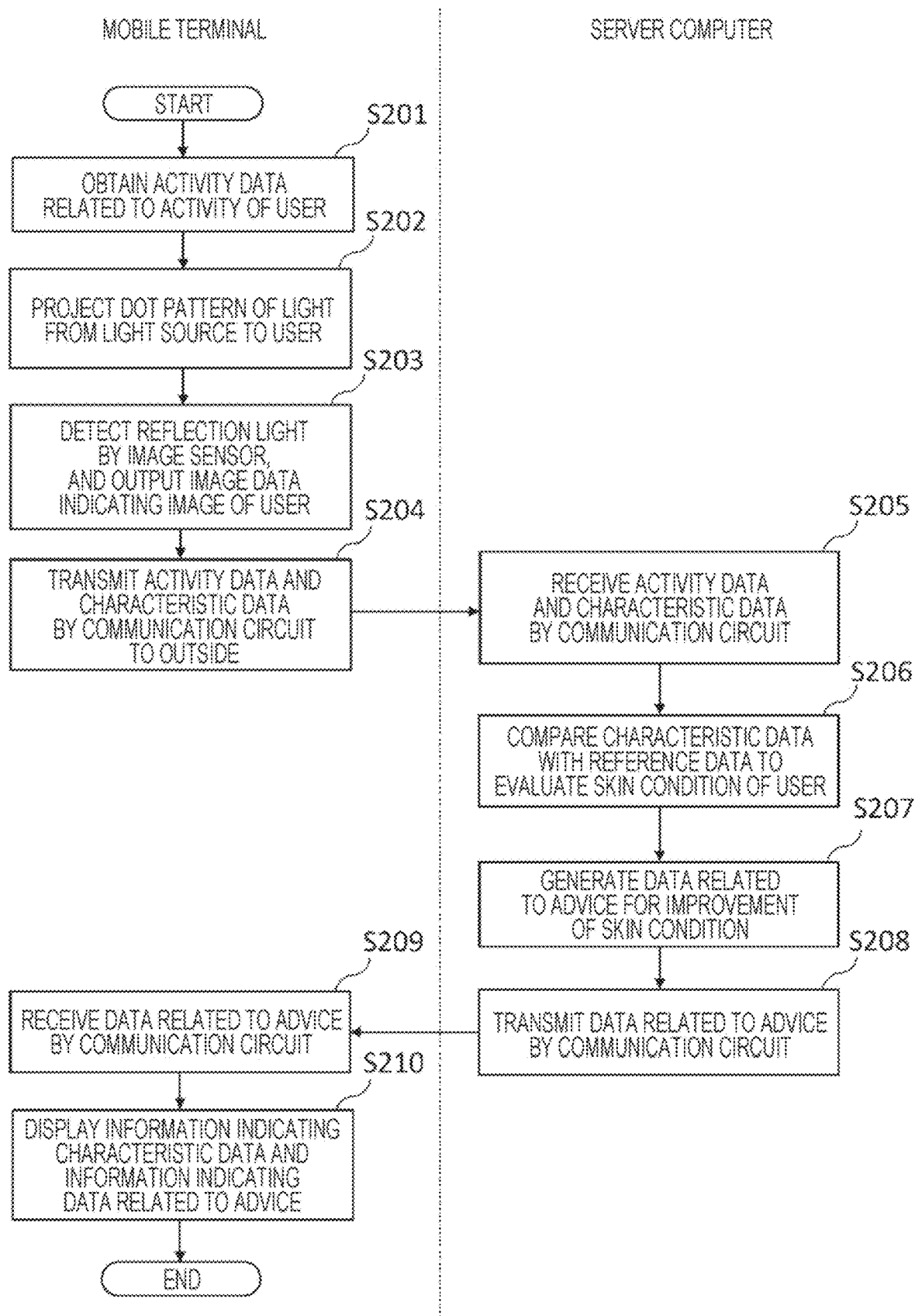
FIG. 13 is a flowchart illustrating the operation of the skin evaluation system in the present embodiment.

FIG. 13 is a flowchart illustrating the above-described operation of the skin evaluation system 200 in the present embodiment. Steps S201 to S204, S209 and S210 show the operation of the mobile terminal 10. Steps S205 to S208 show the operation of the server computer 30.

In step S201, at least one piece of activity data related to at least one activity of the user 3u is obtained. The activity has been recorded since reference data is recorded in the memory 44 until the present time. For instance, the activity is the outdoor activity, sleep, and having a meal. The reference data is characteristic data that characterizes the past condition of the skin 3 of the user 3u.

Steps S202, S203 are the same as steps S101, S102, respectively illustrated in FIG. 8. The arithmetic circuit 22 generates characteristic data from the image data outputted from the image sensor 7 by the same operations as those in S103 to S105 illustrated in FIG. 8, the characteristic data characterizing the current condition of the skin 3 of the user 3u.

The order of step S201 and steps S202, S203 may be reversed.

In step S204, the communication circuit 27 transmits at least one piece of activity data and characteristic data to the outside.

In step S205, the communication circuit 47 receives the at least one piece of activity data and characteristic data.

In step S206, the arithmetic circuit 42 compares the characteristic data with the reference data. The arithmetic circuit 42 compares the current characteristic data with the past characteristic data, and evaluates the change in the condition of the skin 3. For instance, when the skin age obtained from the current characteristic data is higher than the skin age obtained from the past characteristic data, it is evaluated that the condition of the skin 3 has been worsened.

In step S207, the arithmetic circuit 42 generates data related to advice for improving the condition of the skin 3. When the advice is generated, the following processing is performed. The arithmetic circuit 42 determines data related to the change in the condition of the skin 3 from at least one piece of activity data. When the condition of the skin 3 is worsened, a factor of worsened condition may be one or more of the following: increase in the amount of exposure to ultraviolet rays due to a long activity time outdoors, a short sleep time, and insufficient intake of nutrition from meals. As the data related to advice, the arithmetic circuit 42 generates data related to advice suggesting a change in the activity performed by the user 3u based on the determined data. The advice is related to, for instance, reduction in the activity time outdoors, increase in sleep time, and sufficient intake of nutrition.

In step S208, the communication circuit 47 transmits the data related to advice to the communication circuit 27.

In step S209, the communication circuit 27 receives the data related to advice.

In step S210, the display 26 displays information indicating the characteristic data, and information indicating the data related to advice. The information indicating the characteristic data is, for instance, a skin age. The information indicating the data related to advice is, for instance, "reduce the activity time outdoors", "increase sleep time", and "have meals with high nutrition value".

Figure 14B:
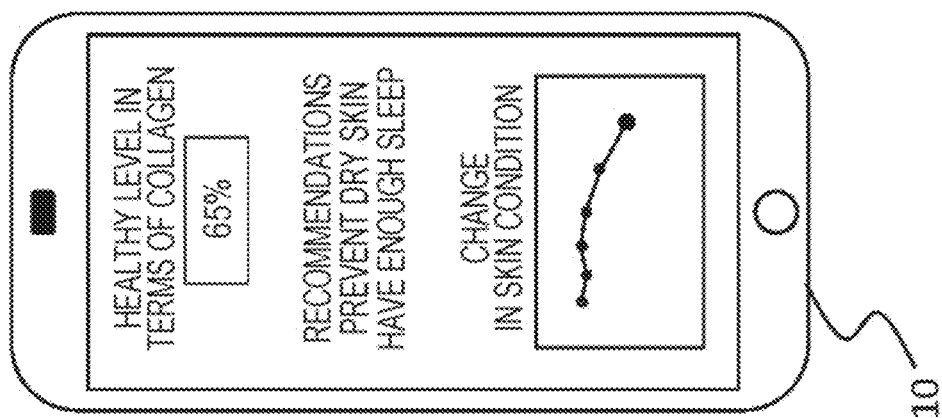
FIG. 14B is a view schematically illustrating an example of application of the skin evaluation system in the present embodiment to a smartphone.
Figure 14A:
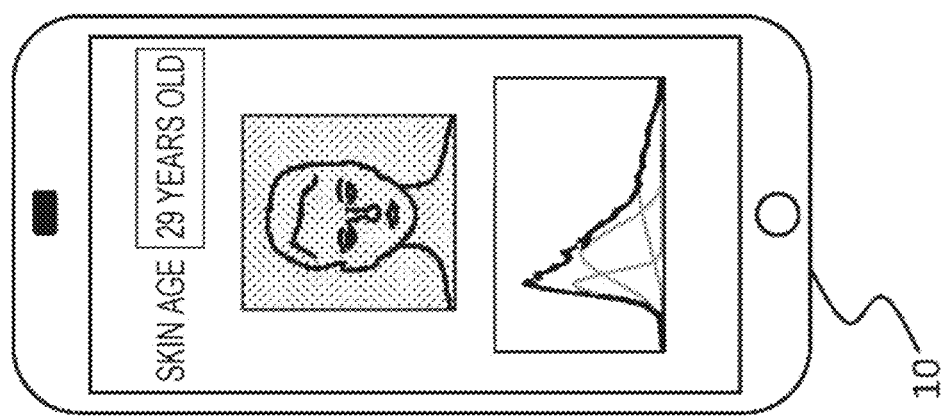
FIG. 14A is a view schematically illustrating an example of application of the skin evaluation system in the present embodiment to a smartphone.

FIGS. 14A and 14B are views each schematically illustrating an example of application of the skin evaluation system 200 in the present embodiment to a smartphone. In the example illustrated in FIGS. 14A and 14B, a function of evaluating the condition of the skin 3 is added, as an application software, to a smartphone provided with the light source 1 that projects a dot pattern created by near infrared laser light, and the camera 2 using near infrared light. When the software is started up, a dot pattern created by near infrared laser light is projected from the light source 1 onto the face of the user 3u, and upon recognition of the face, a near infrared image is captured. In the example illustrated in FIG. 14A, a skin age calculated from the image data is displayed on a screen. As illustrated in FIG. 14B, based on the data accumulated to the server computer 30, change in the condition of the skin 3 so far is displayed by selection on the screen, and an advice on daily life to the user is displayed.

In the example described above, fitting of the frequency distribution with three gaussian distributions is performed, and the condition of the skin 3 is evaluated. It is possible to evaluate the condition of the skin 3 without using the fitting.

Figure 15A:
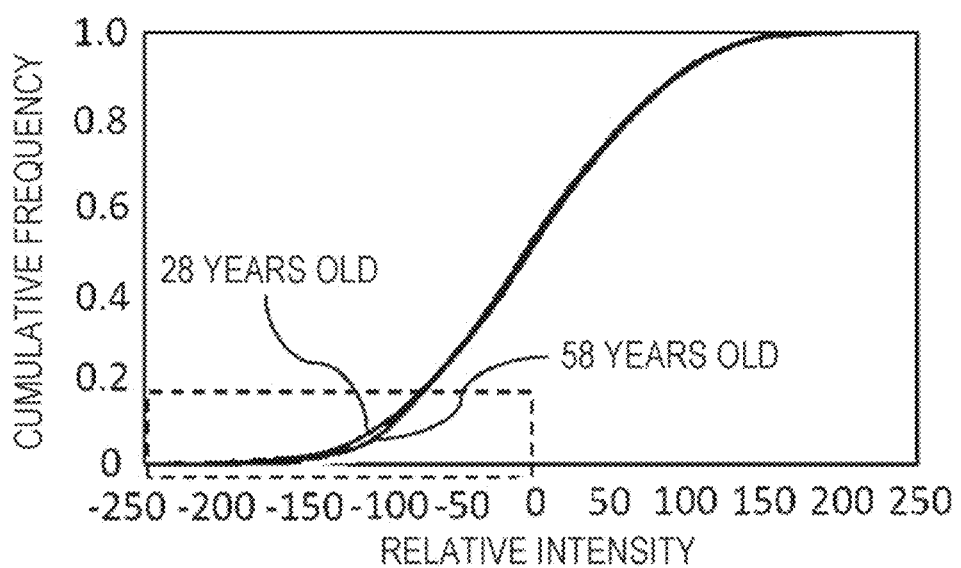
FIG. 15A is a graph illustrating cumulative frequency distributions obtained from users at the age 28 and 58.

FIG. 15A is a graph illustrating cumulative frequency distributions obtained from users at the age 28 and 58. The cumulative frequency distribution shows the relationship between intensity and a cumulative frequency for the intensity or less. In the example illustrated in FIG. 15A, the intensity on the horizontal axis is shifted so that the average value of the intensities of all pixels is 0. In other words, the intensity on the horizontal axis is relative intensity. The cumulative intensity distributions of both users are similar. However, when observed in detail, the user at the age of 28 has a greater dispersion of a portion where an optical intensity is low. This is because the dispersion of the component of the diffuse reflection light L2 within the dermis 34 appears in a portion where an optical intensity is low. The condition of the skin 3 can be evaluated using the distribution.

Figure 15B:
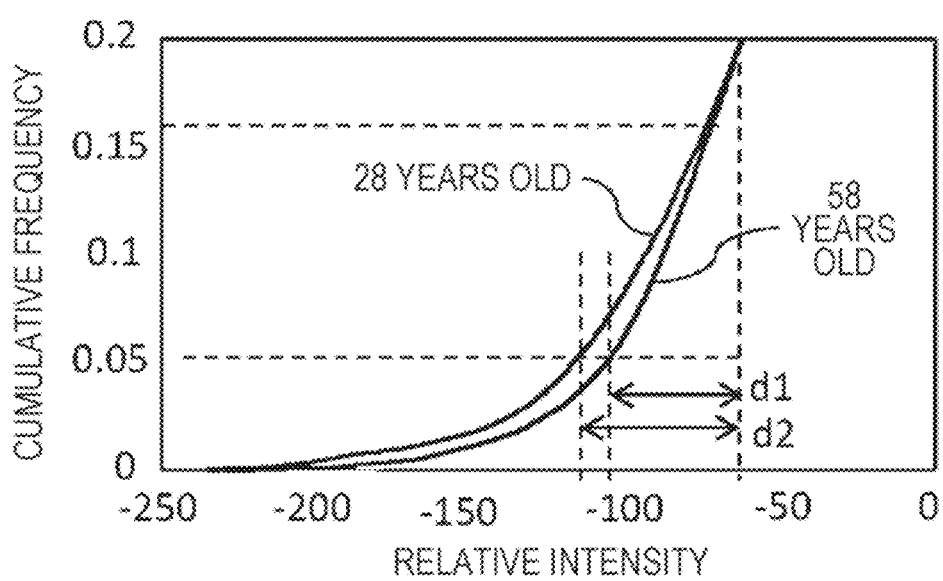
FIG. 15B is an enlarged view of the graph, surrounded by a dashed line illustrated in FIG. 15A.

FIG. 15B is an enlarged view of the graph, surrounded by a dashed line illustrated in FIG. 15A. For instance, a relative intensity for a cumulative frequency of 0.2 is defined as a threshold value, and an integral value for cumulative frequencies for the threshold value or lower is calculated, thus the dispersion of the distribution showing the condition of the skin can be evaluated. The relative intensity for a cumulative frequency of 0.2 is −65. The integral value is the sum of the cumulative frequencies for optical intensity from −∞ to −65. Alternatively, a relative intensity for a cumulative frequency of 0.2 is defined as a threshold value, and the condition of the skin 3 can be evaluated from the differences d1, d2 each between a relative intensity for a cumulative frequency of ¼ of 0.2, that is, 0.05 and a relative intensity for the threshold value.

In the skin evaluation device 100 and the skin evaluation system 200 in the present embodiment, the characteristic data may show a dispersion value in the cumulative frequency distribution of the user 3u. The reference data may show multiple dispersions in multiple cumulative frequency distributions obtained from multiple users. Each of the multiple dispersions is obtained by the same calculation as used to obtain the dispersion in the cumulative frequency distribution of the user 3u. For instance, as the multiple open circles illustrated in FIG. 7, multiple dispersions may be plotted instead of multiple standard deviations. In this case, a linear function may be calculated from the multiple dispersions by the least square method, and a skin age may be calculated from the linear function. Alternatively, the reference data may show a past value of the dispersion in the cumulative frequency distribution of the user 3u.

It is possible to evaluate the condition of the skin 3 by a method other than the method described above. For instance, as illustrated in FIGS. 5A to 5C, the width of the frequency distribution itself is smaller for an older age. The width of the component of the direct reflection light L1 is also smaller for an older age. Unlike the component of the diffuse reflection light L2, the frequency distribution itself and the component of the direct reflection light L1 do not directly reflect the degree of diffuse reflection within the dermis 34. However, the frequency distribution itself and the component of the direct reflection light L1 may indirectly reflect the degree of diffuse reflection within the dermis 34. In this case, the condition of the skin 3 may be evaluated by the standard deviation of the frequency distribution itself and the standard deviation of the component of the direct reflection light L1.

The embodiment of the present disclosure has been illustrated above. The present disclosure is not limited to the embodiment described above, and various modifications are possible. For instance, in the skin evaluation device 100 in the present embodiment, the reference data recorded in the memory 24 may be characteristic data that characterizes the past condition of the skin 3 of the user 3u, in addition to multiple values of standard deviations obtained from multiple users. Thus, the change in the condition of the skin 3 of the user 3u can be checked. Similarly, in the skin evaluation system 200 in the present embodiment, the reference data recorded in the memory 44 of the server computer 30 may be multiple values of standard deviations obtained from multiple users, in addition to characteristic data that characterizes the past condition of the skin 3 of the user 3u. Consequently, the skin age can be calculated by the server computer 30.

The processing explained in the above-described embodiment may be applied to other embodiments. The examples of other embodiments will be described below.

Although a laser light source is used as the light source 1 in the above-described embodiment, another type of light source may be used. For instance, a less expensive LED light source may be used. However, the light emitted from an LED light source tends to spread due to low linearity, as compared with light from a laser light source. Thus, when an LED light source is used, some measures are taken, for instance, a dedicated light collecting optical system is used, or the distance between a target object and the camera is reduced.

The skin evaluation device 100 in the present embodiment may include an adjustment mechanism that adjusts a focal point of an optical system. The arithmetic circuit 22 performs face recognition processing using image data outputted from the image sensor 7. The arithmetic circuit 22 may divide the skin to be measured, such as forehead, nose, cheek, jaw, into areas, and may evaluate the condition of the skin 3 in each area.

The arithmetic circuit 22 may generate data within the epidermis 33 from image data based on the component of the direct reflection light L1 retrieved from the surface of the skin 3, the data including at least one of melanin pigment, presence or absence of fleck, and presence or absence of stigma. A method of separating the component of the direct reflection light L1 is as described above.

As described above, according to the embodiment of the present disclosure, it is possible to evaluate the condition of skin easily without bringing a detection device such as a sensor into contact with a user as well as without using an expensive dedicated facility.

The present disclosure includes a method of performing the operation to be executed by the arithmetic circuit.

The skin evaluation device in the present disclosure is applicable to an application for evaluating the condition of skin easily in a non-contact manner.

What is claimed is:

1. A device comprising:
   a light source configured to project a dot pattern created by a first light onto a skin of at least one user;
   an image sensor configured to detect a second light resulting from the projection of the dot pattern and generate image data which indicates an image of the skin onto which the dot pattern is projected; and
   an arithmetic circuit, wherein:
   the second light includes a component corresponding to light which is scattered inside of the skin, and
   the arithmetic circuit:
      estimates a dispersion degree of intensity of the component corresponding to the light which is scattered inside of the skin based on the image data, and
      generates skin age data that indicates a skin age based on the dispersion degree, the skin age indicating younger age as the dispersion degree increases.

2. The device according to claim 1, wherein the skin age data is related to a condition of the skin within a dermis of the at least one user.

3. The device according to claim 1, wherein:
   the second light includes a first component corresponding to light which is reflected by a surface of the skin and a second component, the second component is the component corresponding to the light which is scattered inside of the skin, and
   the arithmetic circuit separates the first component and the second component based on a relationship between a pixel value in at least a partial area in the image indicated by the image data and a number of pixels having the pixel value in the at least a partial area.

4. The device according to claim 3,
   wherein the arithmetic circuit performed a curve fitting on a curve of a frequency distribution showing the relationship between the pixel value and the number of pixels by a first gaussian distribution, a second gaussian distribution, and a third gaussian distribution,
   an average value of the second gaussian distribution is greater than an average value of the first gaussian distribution, and less than an average value of the third gaussian distribution, and
   the arithmetic circuit separates the second gaussian distribution as the second component.

5. The device according to claim 3,
   wherein the second component corresponds to values of pixels having a value lower than or equal to the pixel value in the at least the partial area.

6. The device according to claim 1, further comprising a display that displays the skin age data.

7. The device according to claim 1,
   wherein the first light has, a wavelength of from 650 nm to 950 nm.

8. The device according to claim 7,
   wherein the light source is a laser.

9. The device according to claim 1, further comprising a polarizing filter disposed between the at least one user and the image sensor,
   wherein the first light is polarized in a specific polarization direction, and
   a polarization direction of light which passes through the polarizing filter is perpendicular to the specific polarization direction.

10. The device according to claim 1, further comprising a bandpass filter disposed between the at least one user and the image sensor,
    wherein a wavelength range of light which passes through the bandpass filter includes a wavelength of the first light.

11. The device according to claim 4, wherein the arithmetic circuit calculates a value of a standard deviation of the second gaussian distribution, and generates the skin age data based on the value of the standard deviation.

12. The device according to claim 11, further comprising a memory that stores reference data to evaluate a condition of the skin, and wherein the arithmetic circuit generates the skin age data based on the value of the standard deviation and the reference data.

13. The device according to claim 12, wherein the at least one user includes a plurality of users,
    the reference data indicates a plurality of standard deviations obtained from the plurality of users, and
    each of the plurality of standard deviations is obtained by a same calculation as used to obtain the standard deviation of the at least one user.

14. The device according to claim 12,
    wherein the reference data indicates a previously obtained value of the standard deviation of the at least one user.

15. A method comprising:
    causing a light source to project a dot pattern created by a first light onto a skin of at least one user;
    causing an image sensor to detect a second light resulting from the projection of the dot pattern and generate image data which indicates an image of the skin onto which the dot pattern is projected, wherein the second light includes a component corresponding to light which is scattered inside of the skin;
    estimating a dispersion degree of intensity of the component corresponding to the light which is scattered inside of the skin based on the image data, and
    generating skin age data that indicates a skin age based on the dispersion degree, the skin age indicating younger age as the dispersion degree increases.

* * * * *